US010138289B2

(12) United States Patent
Renauld et al.

(10) Patent No.: US 10,138,289 B2
(45) Date of Patent: *Nov. 27, 2018

(54) METHOD FOR PRODUCING ANTIBODY USING "NAKED" EXPRESSION VECTOR EXPRESSING TYPE II TRANSMEMBRANE FUSION PROTEIN

(71) Applicant: DELPHI GENETICS SA, Charleroi (BE)

(72) Inventors: Jean-Christophe Renauld, Kraainem (BE); Muriel Lemaire, Ottignies (BE); Laurie Dumoutier, Orbais (BE); Yannick Nizet, Lincent (BE); Alain Vanderplasschen, Tubize (BE); Laurent Gillet, Tenneville (BE); Sophie Scohy, Nivelles (BE); Cédric Szpirer, Fleurus (BE)

(73) Assignee: Delphi Genetics S.A., Sharleroi (Gosselies) (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/988,595

(22) Filed: Jan. 5, 2016

(65) Prior Publication Data

US 2016/0122413 A1 May 5, 2016

Related U.S. Application Data

(63) Continuation-in-part of application No. 13/275,845, filed on Oct. 18, 2011, now Pat. No. 9,234,042.

(Continued)

(51) Int. Cl.
*C12N 15/62* (2006.01)
*C12N 15/79* (2006.01)
(Continued)

(52) U.S. Cl.
CPC ...... *C07K 14/70578* (2013.01); *C07K 14/005* (2013.01); *C07K 14/4747* (2013.01);
(Continued)

(58) Field of Classification Search
None
See application file for complete search history.

(56) References Cited

PUBLICATIONS

Lemaire et al., Anti-cytokine vaccines using living cells presenting endogenous cytokines in fusion with a human transmembrane protein. Cytokine 48(1-2):94, Oct.-Nov. 2009, Abstr PP2-015, Available online Sep. 19, 2009.*

(Continued)

*Primary Examiner* — Claire Kaufman
(74) *Attorney, Agent, or Firm* — Knobbe, Martens, Olson & Bear, LLP

(57) ABSTRACT

Methods are disclosed for generating antibodies and an expression vector used to express protein(s) which provoke the antibody response. The expression vector may be useful in generating an antibody directed to an antigen, comprising a gene in operable linkage with a promoter, which gene encodes upon expressing a fusion protein comprising (i) CD134L, a fragment, homologous or orthologues protein thereof as N-terminal moiety of the fusion protein; and (ii) all or part of an antigenic protein as C-terminal moiety of the fusion protein. To generate the antibodies, the vector is injected into a subject animal, which produces a fusion protein, against which antibodies are generated.

8 Claims, 28 Drawing Sheets
Specification includes a Sequence Listing.

Related U.S. Application Data

(60) Provisional application No. 61/455,278, filed on Oct. 18, 2010, provisional application No. 61/497,107, filed on Jun. 15, 2011.

(51) Int. Cl.
| | |
|---|---|
| C07K 16/28 | (2006.01) |
| C07K 16/24 | (2006.01) |
| C07K 14/705 | (2006.01) |
| C07K 14/47 | (2006.01) |
| C07K 14/005 | (2006.01) |
| C07K 14/54 | (2006.01) |
| C07K 14/715 | (2006.01) |
| C12N 7/00 | (2006.01) |
| A61K 39/00 | (2006.01) |

(52) U.S. Cl.
CPC ...... *C07K 14/5425* (2013.01); *C07K 14/7056* (2013.01); *C07K 14/70575* (2013.01); *C07K 14/7155* (2013.01); *C07K 16/244* (2013.01); *C07K 16/2866* (2013.01); *C07K 16/2875* (2013.01); *C12N 7/00* (2013.01); *A61K 39/00* (2013.01); *A61K 2039/505* (2013.01); *C07K 2317/34* (2013.01); *C07K 2317/73* (2013.01); *C07K 2317/76* (2013.01); *C07K 2319/03* (2013.01); *C07K 2319/40* (2013.01); *C07K 2319/41* (2013.01); *C12N 2710/24134* (2013.01)

(56) References Cited

PUBLICATIONS

Hjelholt et al., IgG subclass profiles in normal human sera of antibodies specific to five kinds of microbial antigens, Pathogens Dis. 67(3):206-213, Apr. 1, 2013.*

UniProtKB Database Accession No. H2Q0M4, TNFSF4 Pan troglodytes (Chimpanzee), Accessed May 3, 2018.*

Compaan, D.M. et al. "The Crystal Structure of the Costimulatory OX40-OX40L Complex," Structure 14, 1321-1330, Aug. 2006.

Yurai, et al., "Vaccines targeting tumor angiogenesis, in Cancer Reviews," New Vaccines, vol. 26, N. Elliot, Ed. (Nova Science Pub.: New York, NY) 2006 p. 53.

Ishii, et al., "OX40 (CD134) and OX40 ligand interaction plays an adjuvant role during in vivo Th2 responses," Eur. J. Immunol. 2003. 33: 2372-2381.

Jenkins, et al., "Dendritic Cell Expression of OX40 Ligand Acts as a Costimulatory, Not Polarizing, Signal for Opitaml Th2 Priming and Memory Induction in Vivo," The Journal of Immunology, 2007; 179:3515-3523.

Baum, et al., "Molecular characterization of murine and human OX40/OX40 ligand systems: identification of a human OX40 ligand as the HTLV-1-regulated protein gp34," The EMBO Journal, 1994, vol. 13 No. 17 pp. 3992-4001.

Yang et al., "DNA versus protein immunisation for production of monoclonal antibodies against Choristoneura fumiferana ecdysone receptor (CfEcR)," Vaccine, 24:3115-3126, 2006.

Morel et al., "DNA immuisation: altering the cellular localisation of expressed protein and the immunisation route allows manipulation of the immune response," Vaccine, 22:447-456, 2004.

Bianci et al. "Maintenance of periperal tolerance through controlled tissue homing of antigen-specific T cells in K14-mOVA mice," J. Immunol. 182(8):4665-4674, Apr. 15, 2009.

Teasdale et al., "The signal for golgi retention of bovine beta1,4-galactosyltransferase is in the transmembrane domain," J. Biol. Chem. 267(6): 4084-4095, Feb. 25, 1992.

Grosenbach et al., "A recombinant vector expressing transgene for four T-cell costimulatory molecules (OX40L, B7-1, ICAM-1, LFA-3) induces sustaind CD4+ and CD8+ T-cell actiation, protection from apoptosis, and enhanced cytokine production," Cellular Immunol. 222-45-57, 2003.

Boyle et al., "Influences of cellular location on expressed antien on the efficacy of DNA vaccination; cytotoxic T lymphocyte and antibody responses are suboptima when antigen id cytoplasmic after intramuscular DNA immunization" International Immunol. 9(12):1897-1906, 1997.

Krippner-Heidenreich et al., "Single-chain TNF, a TNF derivative with enhanced stability and antitumoral activity," J. Immunol. 180:8176-8183, 2008.

Miura et al., "Molecular cloning and characterization of a novel glycoprotein, gp34, that is specifically induced by the human T-cell leukemia virus type I transactivator p40tax," Mol. Cell. Biol. 11(3):1313-1325, Mar. 1991.

* cited by examiner

Fig. 1
A
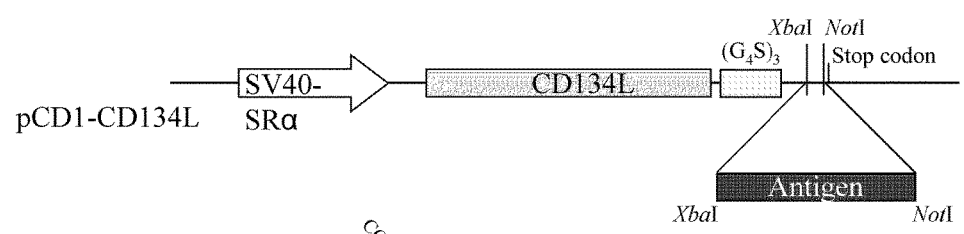
B
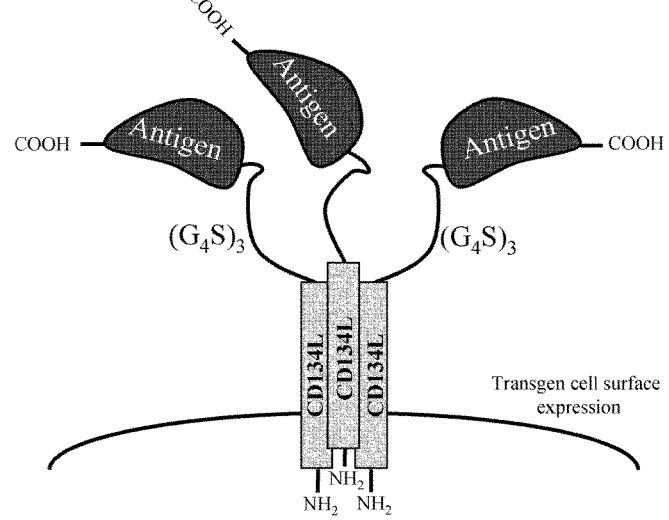

FIG. 6

```
CD134LH        1  --mgrvgqleshvgdsargrf--efnkll-lvasvlgglglllcftyadf
CD134LO        1  --megyrpleenvgnaprgrf--esnkll-ivasvvgslglllclfyvcq
CD134LM        1  megegvnpldenlehgsrgrf--kwkktjrlvvggfkgagmllcflyvcl
CD134LOA       1  --gdvgglgsspakcscejrtpkrpkll-ivsgillwtgilvgliylcv
CD134LAlpa     1  --megrggldggvmntpgrff--lrnkll-ivasvtgglglllcltyfcl CD134LH       46  h-fsaalqyshxyprigsjkvgf---geyk-k--shgfkltsgkedelmkv
CD134LO       46  h-shapeyslqyyplenjstqlqillshece--sdsflltplgkrggtmey
CD134LM       49  q-lssspa--kdgplgxlrgav---trce-d--gqlfissykneyqtmev
CD134LOA      48  dawqgsqdpnghggbnqnllfk----adig-kcssyghltigavngsmkv
CD134LAlpa    46  h-fyg-gvpasypfigsjrvgf---tkce-n--gngftlassnkdgtmky CD134LH       89  gnnsriIncdgfyllslkgyfsqevnlslhyxkdeeplf--qlkkvrsvn
CD134LO       93  gnnsvvlgcdgfyllslkgyfsqeyslslhyrkgesefp--llkktkfan
CD134LM       90  gnnsrvlkcdglylivlkgsffteykldlhfrsdhogislpmlodgrxlv
CD134LOA      94  snplvllpcdgpylvvlkvnsskltlgtirvgngsk-ls--alolsndyd
CD134LAlpa    88  gnnsillscdgfyllslkgyfaqelslslgyrkgrepilf--slskvretyd CD134LH      137  slmyasltykdkyylqvttdrtslddfhvnggelll1hqnggefgvl----
CD134LO      141  snvylklgykdkvylovttdssssckglsvnagglivllgnpgyvcsp---
CD134LM      140  ftvyaslafkdkyyltynapdgloshlqlgndgellvvqltpg-ycspegs
CD134LOA     141  yvtyaslmfkdklslevtdtrcsote--hltg-elghllllapkkvcsnn--
CD134LAlpa   136  fvtgahlafkdlrydnvsthsgtcedlgvnggeltllhgnpggfca----

CD134LH                      ---------   % match
CD134LO                      ---------     63%
CD134LM      186  yhatvnqvpl              40%
CD134LOA                     ---------     35%
CD134LAlpa                   ---------     66%
```

CD134LH : human sequence (SEQ ID NO: 2)
CD134LO : Oryctolagus cuniculus sequence (SEQ ID NO: 26)
CD134LM: Mus musculus sequence (SEQ ID NO: 27)
CD134LOA: Ornithorhynchus anatinus sequence (SEQ ID NO: 29)
CD134LAlpa: Vicugna pacos sequence (SEQ ID NO: 28)

The amino acid residues are underlined when at least 3 corresponding amino acid over the 5 different sequences are identical.

FIG. 7

```
CD134L Human      1  atggaaggg------tccaacttctggagaga-atgtggaaatgca-
CD134L Rabbit     1  atggaaggg------tccgaccctagaagaga-atgtggaaacgca-
CD134L Mouse      1  atggaaggggaagggttcaacccctggatgaga-atctggaaacgga-
CD134L Alpaca     1  atgcaaggg------tccaacccctggacggga-atgtggaaacacg-
CD134L Platypus   1  atggatgttg------gacagcctgtggagagagcctgcaagtgtga CD134L Human     43  ----gccagtccagatccgagagaacaag---ctattactgttgcct
CD134L Rabbit    43  ----ccaaggccaagtttgagagaaacaag---ctattactgttggct
CD134L Mouse     49  ----tgaaggccaagattcaagtggaggagacgctaaggctggtgtct
CD134L Alpaca    43  ----ccaaggggagattcttaaggaacaag---ctattactgttgcct
CD134L Platypus  45  atgtgaaggagaactccaagaggaccgaag---gttctgctggtgcct CD134L Human     86  gtgtaattgaggactggggctgctcatgtgcttgacctacatctgctg
CD134L Rabbit    86  ccgtagttgagcactgggctgctttgtgcctcacctagctgccag
CD134L Mouse     95  gtggatgaggggagcaggatgcttgtgttcttcatctgtctggctg
CD134L Alpaca    86  gcgtaattgagggctggggctgctgttgtgctactacatctgtctg
CD134L Platypus  92  gcatcctgctgtggtgaggttgcttgtgtgcctgatctacatctgctgg CD134L Human    136  cactgtct---ggtcttcaggtatcacatcggtatcc-------tcg
CD134L Rabbit   136  cgctcgcat---ggtcccgaggtgtcactttagtatct-------tcc
CD134L Mouse    145  cgactgtct---tgctctgcggca------aaggacgg-------tcc
CD134L Alpaca   136  cacttgtat---gc----tcaggtgccagctgagtacc-------tcc
CD134L Platypus 142  gatgcctgcaggttctcaggacccaaatgggcatccaggggccatca CD134L Human    174  aattcaagtatcaaagtacaattaccggatataagaag--------
CD134L Rabbit   174  aattgaaatatcatgacactacctt--gaagcttgacgtccatgagtg
CD134L Mouse    177  aatcaagactcagagtagcagttactagatgtgaggat---------
CD134L Alpaca   171  aattcaagtatcgagtacagttttaccgaaggtgaaagt---------
CD134L Platypus 192  gaacctaattttaaagcagatatt--ggaaagtgtgaat---------

CD134L Human    214  ----gagaaggttttcatgctcagttgcaaaggaggatgaagttattga
CD134L Rabbit   222  tgagaggacagtttcatgctccgactgtaaaaaggacggaaccatgg
CD134L Mouse    217  ----gggcaactattcatgagctgatagaagatgagtatcaaactatgg
CD134L Alpaca   211  ----gagaatggtttctcgcattgcatcgtcaacaaggatgggaccatga
CD134L Platypus 230  ----ccggtgggaatca-gttaagcatgcagctgttaagcagtccatga CD134L Human    260  agtgcagaagcaactcagtcatcatcaactgtgatggtttatctgatc
CD134L Rabbit   272  aagtgaaaacaactcagtcgtcatccagtgtgatggctttatctctg
CD134L Mouse    263  agtgcagaagaattggttgtcatcaagtgcgatggctttatatgatc
CD134L Alpaca   257  aggtgaaaacaactcaattgatcatcagctgtgacggcttctatctgatc
CD134L Platypus 275  agtgagaaacaacttgctcctcatcccttgtgatggtctttattggtc CD134L Human    310  tcctgaagggctacttctcccaggaagtcaacattagccttcattaca
CD134L Rabbit   321  tctctgaaggctactcctccaggaggtcagcattagtcttactatcg
CD134L Mouse    313  tactgaaggctccttttccaggaggtcagatgaactgcattccg
CD134L Alpaca   307  tcctgaaggctacttctctaggagctcagctcgcttcagttacg
CD134L Platypus 325  tagctgaagtcactcgtcaagctcctcacaatacgattcgctatcg CD134L Human    360  gaaggatgaggagccctct----tgcaa--ctgaa-gaaggtg--ggt
CD134L Rabbit   372  gaaggtgaggggcttttgc----cgatc--gtgaa-gaagacg--aagt
CD134L Mouse    363  gaaggatcataatgccatgtctattgcaatggtgaacgatggtggaagga
CD134L Alpaca   357  gaaggtcgggagccctct----tgtcc--gtaag-caaggtg--agaa
CD134L Platypus 375  caaggcgaaaag---ctct----ccggcc--ttgaa-tctctcgg--aacg
```

FIG. 7 (Continued)

```
CD134L Human      401 ctgtcaactccttgatggtggcctctctgacttacaaagacaaagtctac
CD134L Rabbit     413 ttgccaactccaacgtggtgttaaaattggggttacaaagacaaagtctac
CD134L Mouse      413 ttgt---cttcactgtggtggcctctttggctttcaaagataaagtttac
CD134L Alpaca     398 ctgtcgacttcgtcacagtggcccatctggctttcaaggacatagtctac
CD134L Platypus   413 atgtggattacgtcacagtggcttccctcatgttcaaggacaagctctcc CD134L Human      451 ttgaatgtgaccactgacaat---acctccctg-gatgac-ttccatgtg
CD134L Rabbit     463 ctgaatgtgaccaccgacagc---gcctcctgc-aagcag-ctcagtgtg
CD134L Mouse      460 ctgactgtaaatgctcctgat---a-ctctctgcgaacac-ctccagata
CD134L Alpaca     448 ttgaatgtgagcactcacagt---accacctgt-gaagac-atccaggtg
CD134L Platypus   463 ctggaagtg---actgacaccgcaactgcact-gagcacattacaggtg CD134L Human      496 aatggcggagaactgattcttat----ccatcaaaatcctggtgaattct
CD134L Rabbit     508 aatgctggggagctgattgtcat----ccttcaaaatcccggtgggtact
CD134L Mouse      505 aatgatggggagctgattgttgt----ccagctaacgcctgg---atact
CD134L Alpaca     493 aatggtggggaactgactctcat----tcatcaaaatcccggtggattct
CD134L Platypus   509 aa----ctaggcctcattttgctggcacccaaaaagtactgcagcaacaa CD134L Human      542 gtgtcctt-----------------------------------
CD134L Rabbit     554 gcgctccc-----------------------------------
CD134L Mouse      548 gtgctcctgaaggatcttaccacagcactgtgaaccaagtaccactg
CD134L Alpaca     539 gtg--ct-----------------------------------
CD134L Platypus   555 c-----------------------------------
```

CD134L Human: human sequence (SEQ ID NO: 1)
CD134L Rabbit: Oryctolagus cuniculus sequence (SEQ ID NO: 22)
CD134L Mouse: Mus musculus sequence (SEQ ID NO: 23)
CD134L Alpaca: Vicugna pacos sequence (SEQ ID NO: 24)
CD134L Platypus: Ornithorhynchus anatinus sequence (SEQ ID NO: 25)

The nucleic acids are underlined when at least 3 corresponding nucleic acid over the 5 different sequences are identical.

% Identities:

| Sequence | Start | End | Match* | NonMatch** | %Match |
|---|---|---|---|---|---|
| CD134L Human | 1 | 549 | | | |
| CD134L Rabbit | 1 | 561 | 422 | 141 | 74 |
| CD134L Mouse | 1 | 594 | 396 | 211 | 65 |
| CD134L Alpaca | 1 | 543 | 437 | 112 | 79 |
| CD134L Platypus | 1 | 555 | 312 | 263 | 54 |

Note: Match* and NonMatch** represent the number of nucleic acids identical to or different from the human CD134L nucleic acids, respectively.

FIG. 9
Platypus CD134L
9A - Staining with unspecific sera:
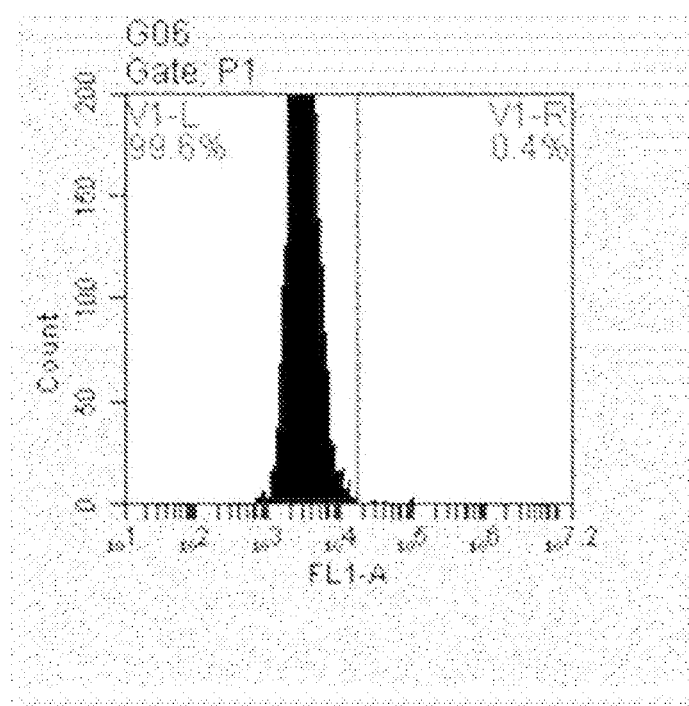
9B - Staining with anti-CD134LOA specific antibody:
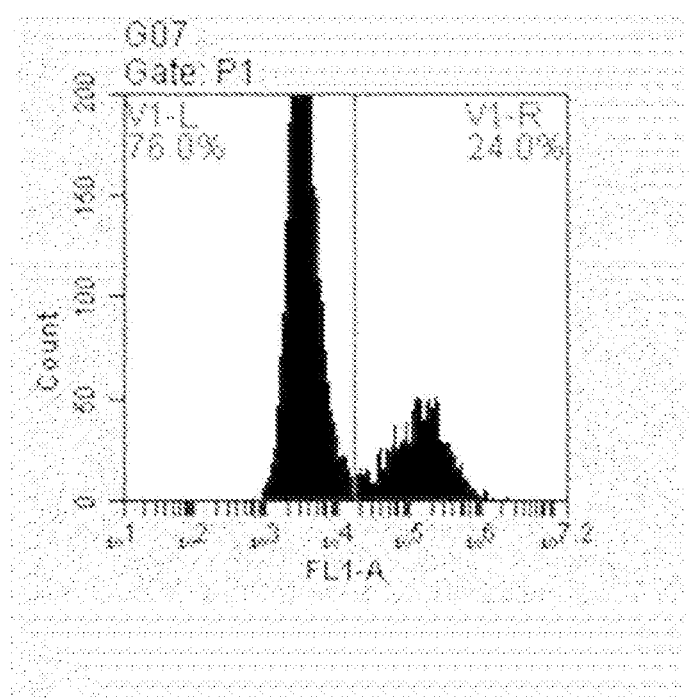

FIG. 9 (continued)
Human CD134L
9C - Staining with unspecific sera
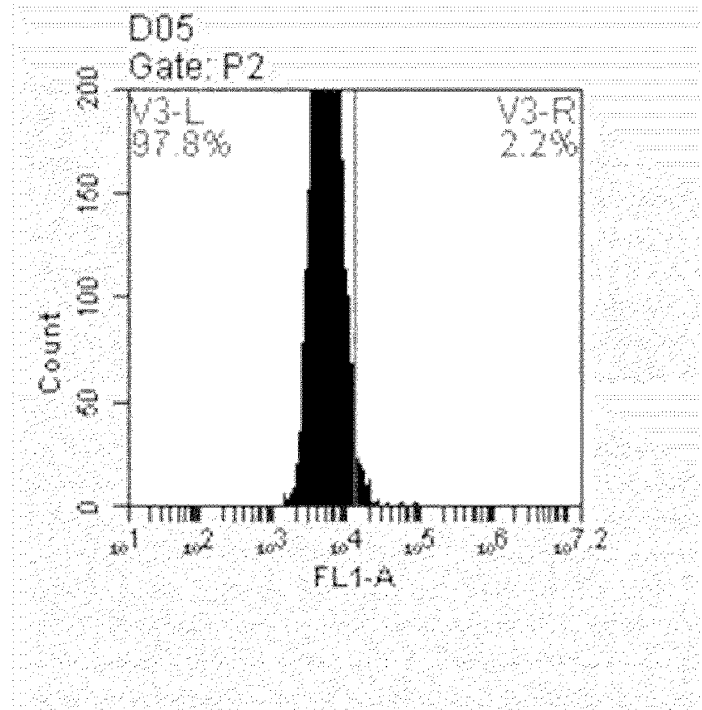
9D - Staining with anti-CD134LH specific antibody
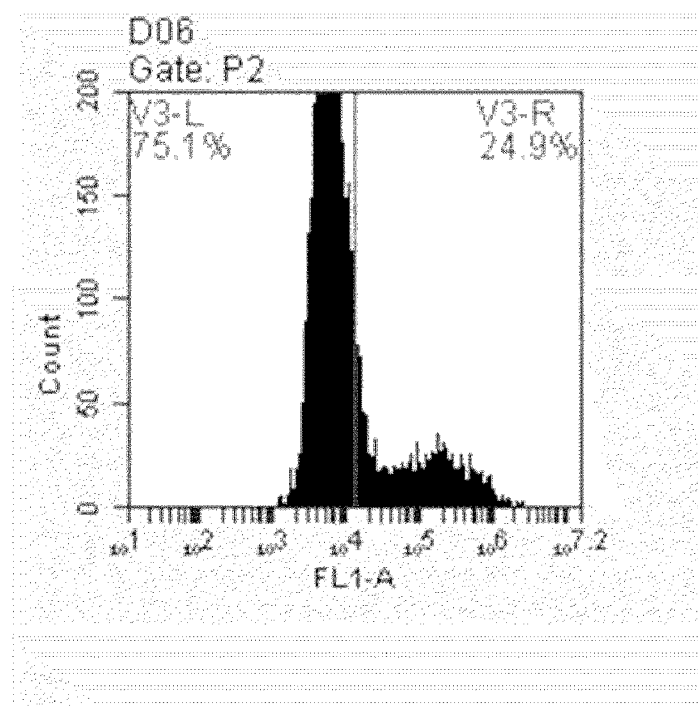

FIG. 9 (continued)
Mouse CD134L
9E - Staining with unspecific sera
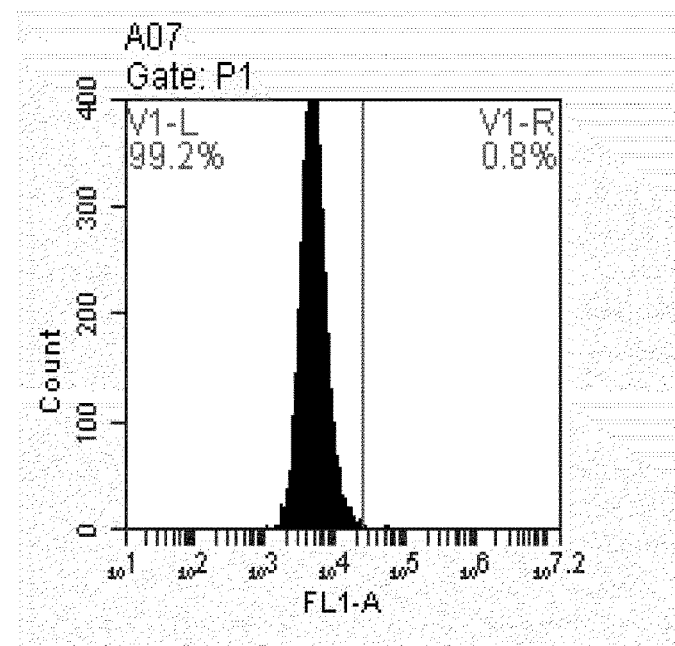
9F - Staining with anti-CD134LM specific antibody
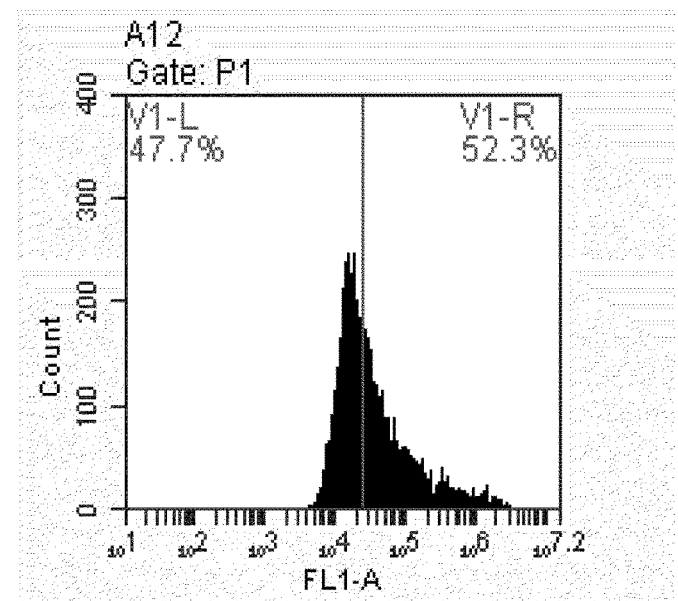

FIG. 9 (continued)
Rabbit CD134L
9G - Staining with unspecific sera
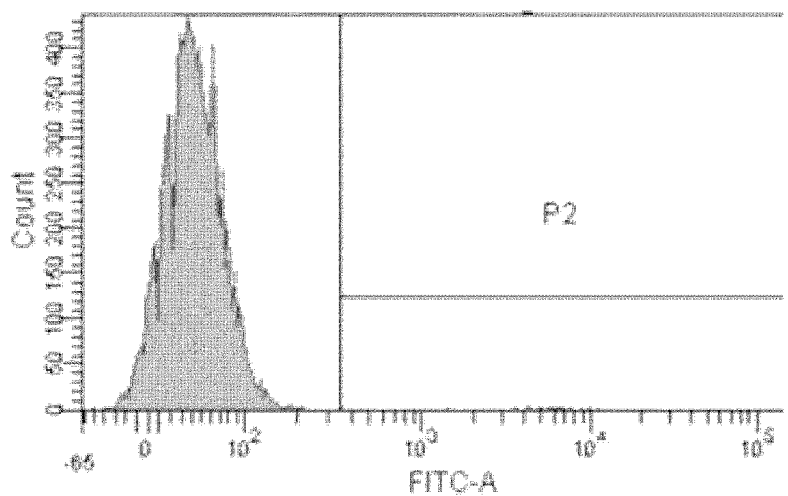
9H - Staining with anti-CD134LO specific antibody
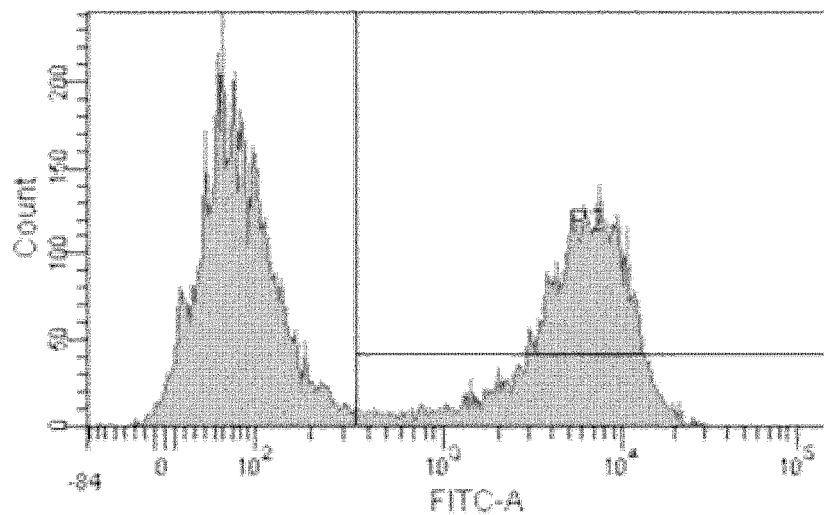

FIG. 9 (continued)
Alpaca CD134L
9I - Staining with unspecific sera
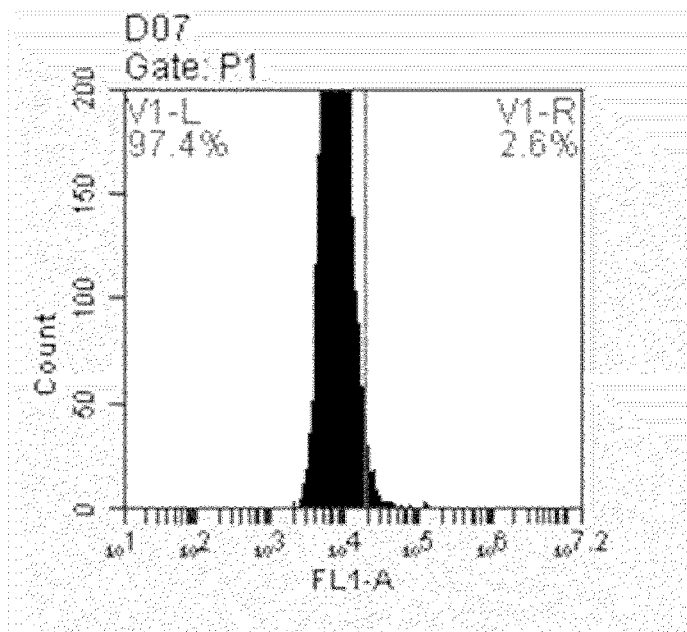
9J - Staining with anti-CD134LAlpa specific antibody
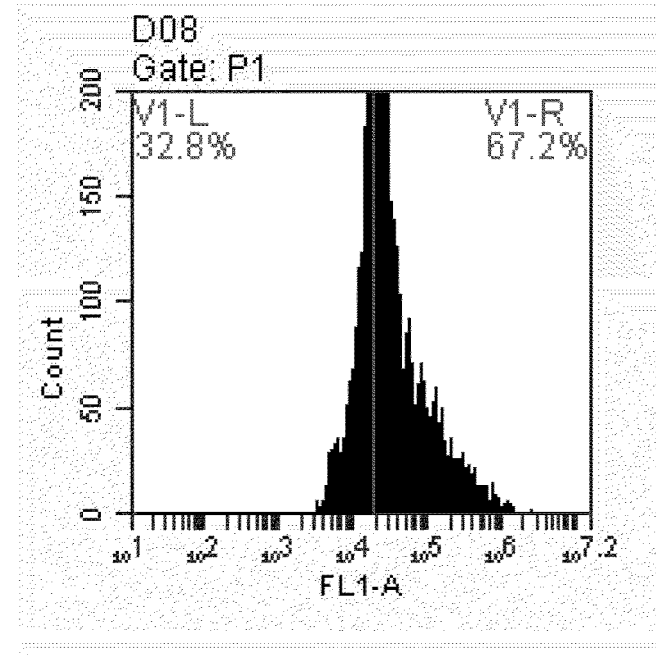

FIG. 10
10A - Negative control
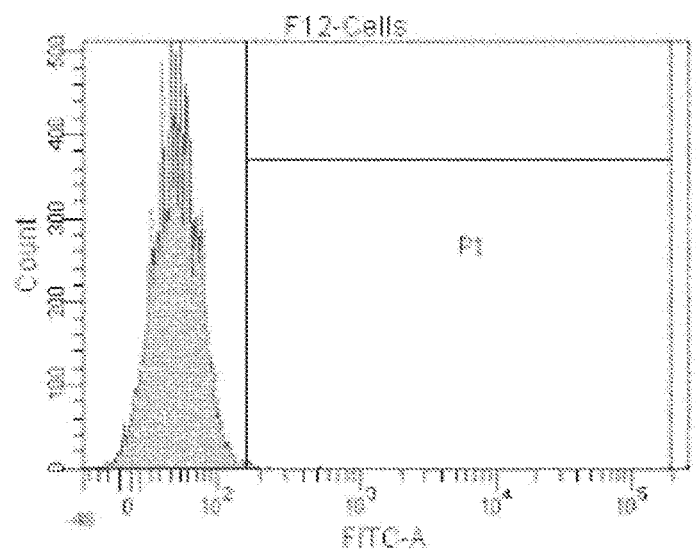
10B - NIH3T3 cells expressing CD134L from Mus musculus + (GGGGS)$_3$ + antigen
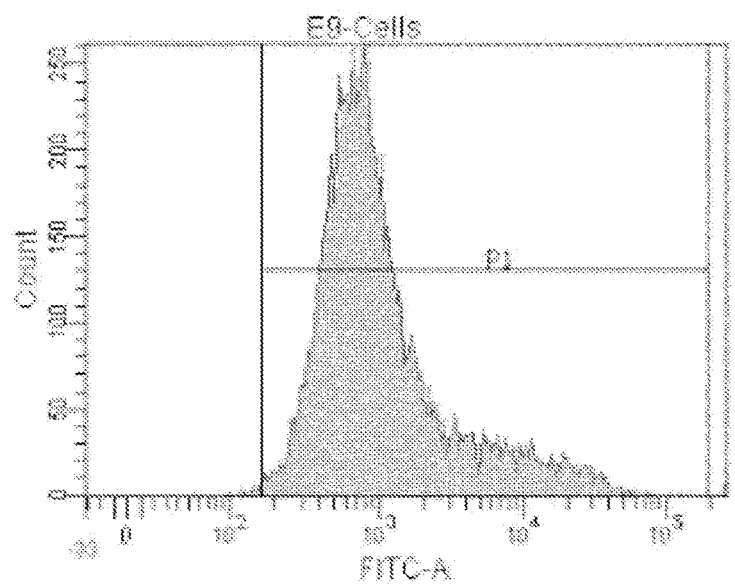

10C - NIH3T3 cells expressing CD134L from Oryctolagus + (GGGGS)3 + antigen

FIG. 11
11A - Negative control
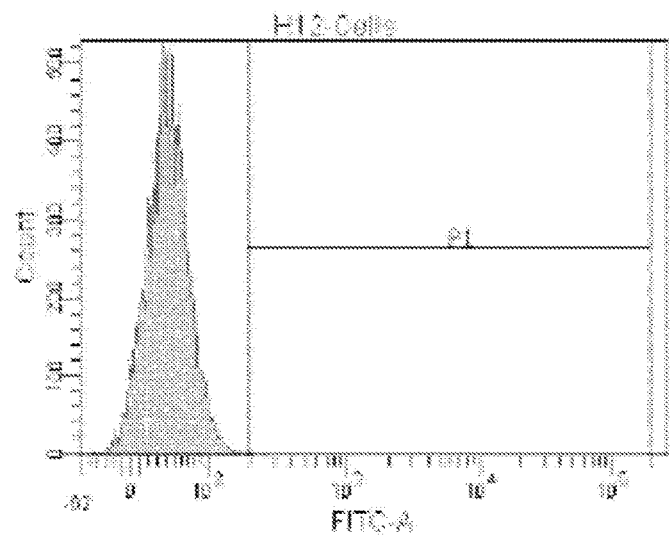
11B - NIH3T3 cells transfected with the vector encoding the CD134L from Mus musculus+ (GGGGS)$_3$ + antigen
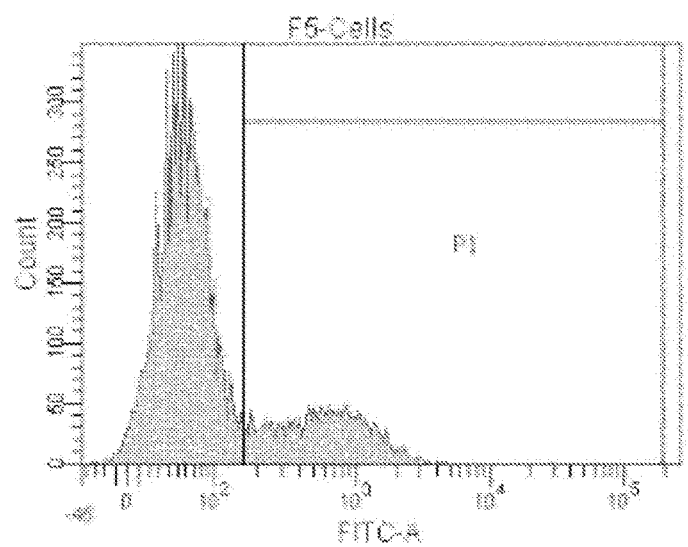

11C - NIH3T3 cells transfected with the yector encoding the CD134L from Ornithorhynchus + (GGGGS)$_3$ + antigen 12A - Negative control:

| Plot 2: A12; Gated on P1 | Count | Events / µL | % of This Plot | % of All | Mean FL1-A | CV FL1-A | Median FL1-A |
|---|---|---|---|---|---|---|---|
| This Plot | 5,000 | 1250 | 100.00% | 86.54% | 5,136.27 | 457.38% | |
| V1-L (1.0 / 14,721.0) | 4,961 | 1240 | 99.22% | 85.86% | 3,968.45 | 42.85% | |
| V1-R (14,721.0 / 16,777,215.0) | 39 | 10 | 0.78% | 0.67% | 153,688.82 | 142.77% | |

12B - CHO cells transfected with the Ornithorhynchus vector encoding the antigen (307 amino acids of a human receptor protein)

| Plot 2: A03:<br>Gated on P1 | Count | Events /<br>µL | % of This<br>Plot | % of All | Mean FL1-A | CV FL1-A | Median FL1-A |
|---|---|---|---|---|---|---|---|
| This Plot | 5,000 | 714 | 100.00% | 92.01% | 52,781.39 | 226.83% | |
| V1-L (1.0 /<br>14,721.0) | 957 | 137 | 19.14% | 17.61% | 11,599.29 | 19.32% | |
| V1-R<br>(14,721.0 /<br>16,777,215.0) | 4,043 | 578 | 80.86% | 74.40% | 62,529.42 | 209.92% | |

12C - CHO cells transfected with the alpaca's vector encoding the same antigen

| Plot 2: A02: Gated on P1 | Count | Events / µL | % of This Plot | % of All | Mean FL1-A | CV FL1-A | Median FL1-A |
|---|---|---|---|---|---|---|---|
| This Plot | 5,000 | 833 | 100.00% | 91.52% | 41,177.94 | 177.24% | |
| V1-L (1.0 / 14,721.0) | 1,505 | 251 | 30.10% | 27.55% | 11,161.95 | 21.16% | |
| V1-R (14,721.0 / 16,777,215.0) | 3,495 | 583 | 69.90% | 63.98% | 54,103.28 | 155.34% | |

FIG. 13

```
CD134LOA        1  mdvgqpl----geapskcecergtpkrpklffyssillwiqllvqliyiq
CD134LAlpa      1  megvqpldgrvgntpg------rrflrnkllvasvlqqlqfllelryld CD134LOA       47  wdawgasqtpnghpgghqnlifkadigkcesggnblrigavng--smkye
CD134LAlpa     45  lhfy--agvpaeypplqs---irvqftkgen-engftlassnkdgtmkyq CD134LOA       95  nhlvlipddpyfvyikvhsskltititirymg-eklssinlsodydyvt
CD134LAlpa     89  nhsllsrdgfylslkgyfqqekslslqyrkgrsplfslskvrtydfrt CD134LOA      144  yasimfkdklslsyrdtrnctqhlt---gelglillagkkypsnn
CD134LAlpa    139  yahlsfkdlvylnysthsttcediqvnggeltlihqpgqfga--
```

CD134LOA: Ornithorhynchus anatinus sequence (SEQ ID NO: 29)
CD134LAlpa: Vicugna pacos sequence (SEQ ID NO: 28)

The amino acid residues are underlined when at least 3 corresponding amino acid over the 5 different sequences are identical.

FIG. 14

```
CD134LOA     1  --mdvqgl-----gepakcecerxtpkrpklllysgillwlgllvellv
CD134LAlpa   1  --mgvgglddgnvgatpg------rrflrnkllyasviqglgllllglty
CD134LH      1  --mervgnl----eenvq--naafprfernklllyasviqglgllllgfty
CD134LO      1  --megvrglleenvgnap-------rpcfernklllyasvvqslgllclty
CD134LM      1  mgqsgvgnl----denlengsrpgfkwhktlrivysgik-gsgmllgfly CD134LOA    45  lcwdawgasgdgn----ghgoghqnlifkadl---gkeesggnbltlqavn
CD134LAlpa  43  lclhfy--agvpa----eypplqe---lrvqf----tkcen-sngftlsssn
CD134LH     43  lclh-fsalgvsh----ryp-rlqslkvqfte---ykkek-gflltsqked
CD134LO     43  vg-----ghshapevslqyg-pleolstqlqlltshecaedsflplqkrd
CD134LM     46  vg----lglssspa----kdsplgr----lrgav---trcadg--qlflssyk CD134LOA    89  ---q---sakvennlvllpedgpylvyLkvhagklltlrlryeng-ek-ls
CD134LAlpa  91  ---kdgtmkvqnnsllisodgfylslkgyfagelalslqvrkgrep-lf
CD134LH     84  ----s----lmkvqnnsvllnedgfylslkgyfaqevalslhyqkd-gepll
CD134LO     88  ---g---tmevqpnsvvlqedgfYlslkgyfaqevalslhyqkg-gepfp
CD134LM     82  neyq--tmevqnnsvvlkedglylivylkgsffqevkldlhfred-hn-pl CD134LOA   132  alnlsnd----ydyvtgaalmfkdhlsleyt-drrnctg---hlt----g-el
CD134LAlpa 127  slskvrt----ydlvtgahlafkdlvylngs-tnsttce---dlqvngg-el
CD134LH    128  qlkkvrs----vnslmwasltykdkvylnyt-tdntslqddffyn---gosl
CD134LO    132  lljkktkf----ansnvglklgykdkvylnyttdsascka--lsvna-g-el
CD134LM    129  slpmlndgrrlvftvvaslafkdkvyltvn-apdtlcg--hlqiedg-el CD134LOA   172  qlillapkkycsnn------------  %Match
CD134LAlpa 170  tllogngqgfcs--------------  38%
CD134LH    171  llioqnggefgvl-------------  37%
CD134LO    175  lvflqnpggycap-------------  35%
CD134LM    174  lvvqltg-gycapegsyhstvnqvpl 29%
```

CD134LH : human sequence (SEQ ID NO: 2)
CD134LO : Oryctolagus cuniculus sequence (SEQ ID NO: 26)
CD134LM: Mus musculus sequence (SEQ ID NO: 27)
CD134LOA: Ornithorhynchus anatinus sequence (SEQ ID NO: 29)
CD134LAlpa: Vicugna pacos sequence (SEQ ID NO: 28)

The amino acid residues are underlined when at least 3 corresponding amino acid over the 5 different sequences are identical.

FIG.15
15A - Negative control
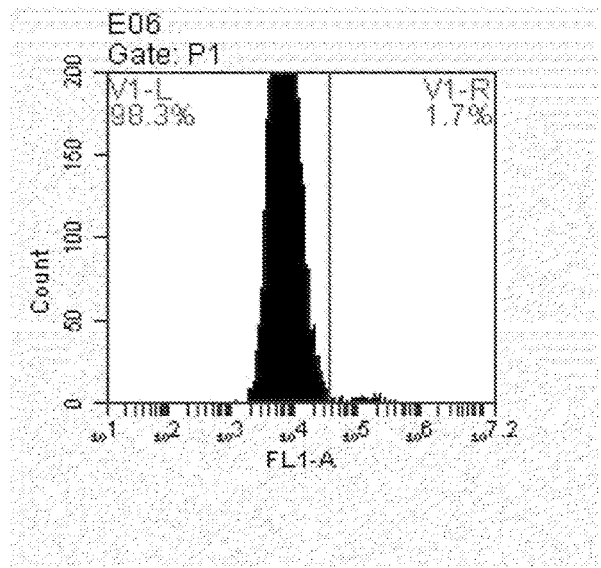
15B - CHO cells transfected with the Ornithorhynchus vector encoding the antigen 2 (231 amino acids of a human proteoglycan)
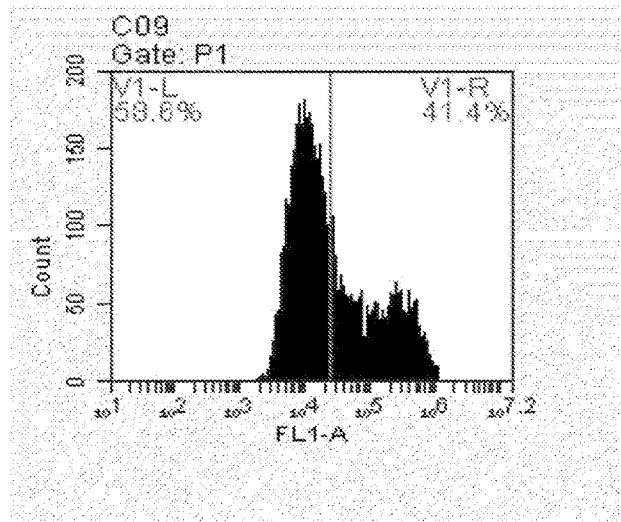

FIG. 16
16A – Negative control
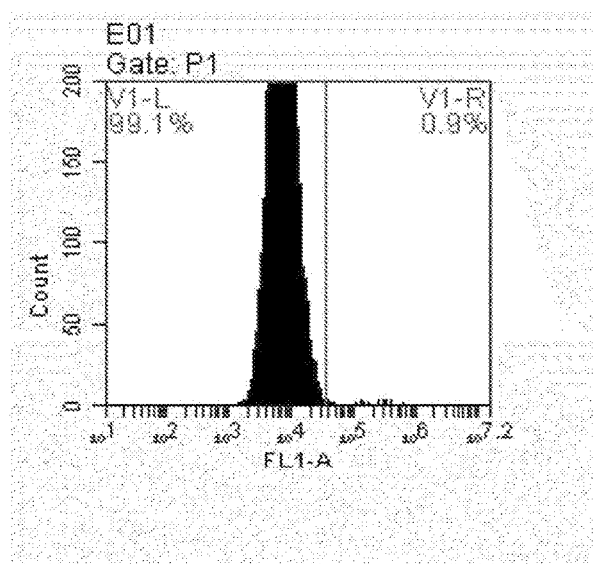
16B - CD134LM + (GGGGS)₃ + antigen 1 (66 amino acids from human transmembrane protein)
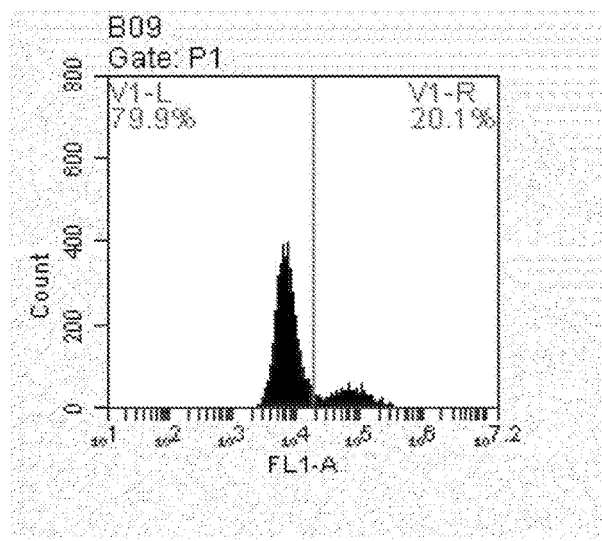

FIG. 16 (continued)
16C - CD134LM+ (GGGGS)$_3$ + antigen 2 (174 amino acids from human muscarinic receptor)
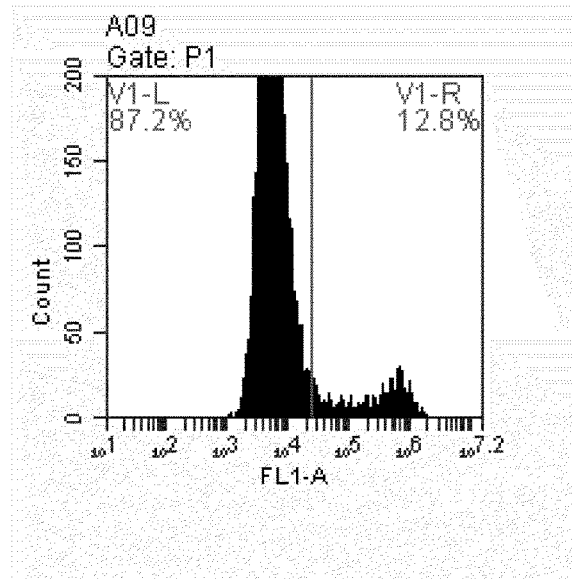
16D - CD134LM + (GGGGS)$_3$ + antigen 3 (135 amino acids of a human protein expressed by neuronal precursor cells)
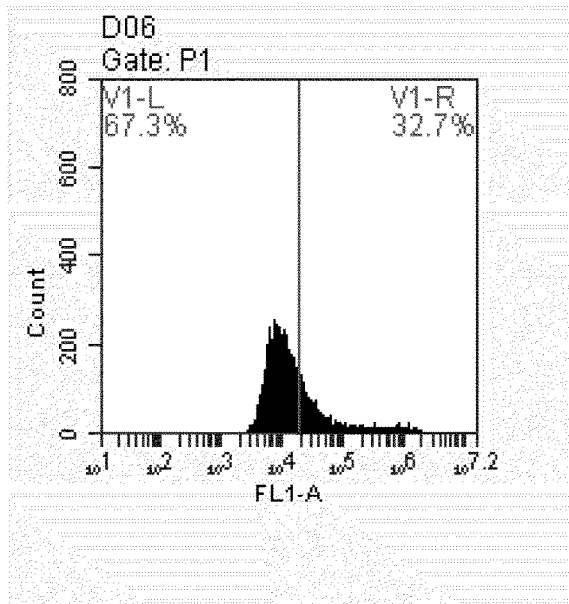

FIG. 17
17A - Negative control
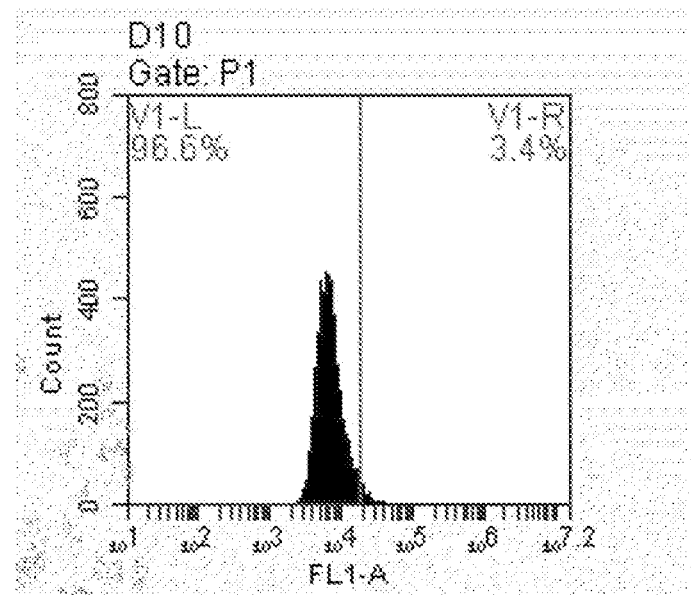
17B - CD134L + (GGGGS)₃ + antigen
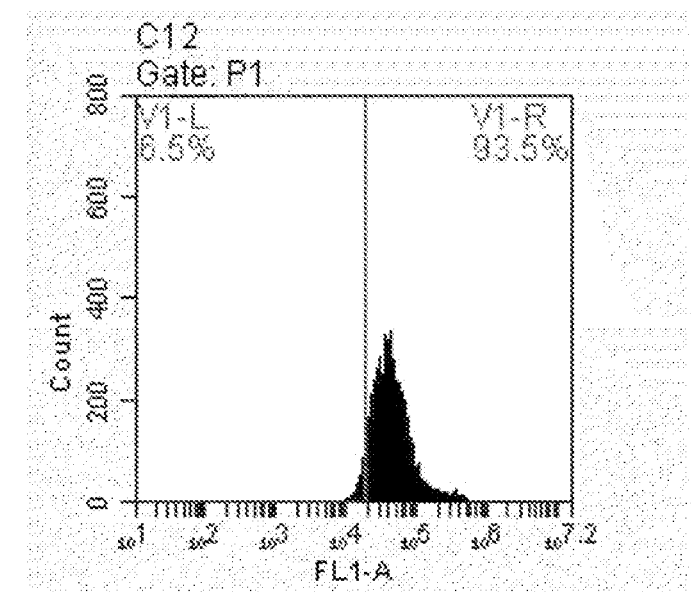

17C - CD134L + antigen (no linker)

METHOD FOR PRODUCING ANTIBODY USING "NAKED" EXPRESSION VECTOR EXPRESSING TYPE II TRANSMEMBRANE FUSION PROTEIN

CROSS-REFERENCE TO RELATED APPLICATIONS

This application is a Continuation-in-Part Application of U.S. application Ser. No. 13/275,845, filed Oct. 18, 2011, which claims the benefit of U.S. Provisional Application No. 61/455,278 filed Oct. 18, 2010 and of U.S. Provisional Application No. 61/497,107 filed Jun. 15, 2011 each incorporated by reference in its entirety.

REFERENCE TO SEQUENCE LISTING

The present application incorporates by reference the sequence listing submitted as an ASCII text filed via EFS-Web. The Sequence Listing is provided as a file entitled SEQ.txt, created on Dec. 30, 2015, which is 16.1 Kb in size.

FIELD OF THE INVENTION

The invention of the present application relates to a method for producing an antibody by gene immunization. More specifically, the invention relates to a method of enabling easy production of an antibody useful as drugs, diagnostic agents, reagents for the research, etc., and to an expression vector used in this method.

BACKGROUND AND PRIOR ART OF THE INVENTION

Since the development of recombinant DNA techniques in the late 1970s, gene fusion technology has been used for generating multifunctional proteins for a broad range of applications. Fusion proteins are utilised in protein science research for diverse applications. In order to construct such fusion proteins, two types of connection are possible. One is 'end to end' fusion in which the N-terminus of one domain is linked to the C-terminus of the other domain. The second is "insertional" fusion in which one domain is inserted in-frame into the middle of the other parent domain.

Antibodies have widely been utilized as reagents for the research for the purpose of detection, purification, elimination, inhibition of a protein or the like, because it has property of recognizing specific protein and binding thereto. Recently, it has widely been used not only as reagents for the research but also as drugs or diagnostic agents.

In producing antibodies, it has so far been general to use a method that a large amount of protein as an antigen is purified and injected to an animal or animals such as rabbits or mice to collect antibodies generated in sera. It required, however, much time and a great deal of labor to obtain a large amount of a purified antigenic protein. It is desired to provide a more convenient method for producing antibodies, accordingly.

It was reported that when a gene coding for an influenza virus nucleoprotein is integrated into an expression vector and intramuscularly injected directly as DNA to mice, then virus proteins are produced in the murine bodies and additionally the antibody against these proteins are generated in the sera (Ulmer et al., *Science* 259: 1745-1749, 1993). As a result, this expression vector received much attention for the use to produce antibodies. Thus, it has been designated as gene immunization that an expression vector for an antigenic protein is inoculated directly to an animal to generate and prepare antibodies. In using gene immunization, however, in some cases, the titer of the generated antibody is very low or no antibody is generated depending on the kind of the antigen used.

It was reported as an example of gene immunization that ovalbumin was fused in the downstream of transmembrane domain of transferrin receptor to form a membrane type and it was injected intramuscularly or subcutaneously to mice in order to investigate an effect of the expression site of antigenic protein on the efficacy of gene immunization. The titer of the antibodies generated, however, rather decreased since the protein was converted into a membrane type. (Boyle et al., *Int. Immunol.* 9: 1897-1906, 1997).

The document EP 1 304 375 refers to a method for producing an antibody against an antigenic protein, wherein the antigenic protein is fused with the C-terminal side of a transmembrane domain of which the N-terminal side is located in the cell and the C-terminal side is out of the cell and the fusion protein is inoculated in a non-human animal.

The purpose of the invention of the present application is to provide an improved method for producing antibodies directed to proteins, for which it was difficult to produce antibodies in so far known gene immunization methods.

Additionally, the purpose of the invention is to provide an expression vector useful to express an immunogen which is applied in the above-mentioned method for producing an antibody.

How these and other aspects of the invention are achieved will be seen from the disclosure which follows.

SUMMARY OF THE INVENTION

In one embodiment, an expression vector useful in generating an antibody directed to an antigen is provided. The expression vector comprises a gene in operable linkage with a promoter, which gene encodes a fusion protein upon expression. The fusion protein comprises:
  (i) CD134L, a fragment or homologous protein thereof as N-terminal moiety of the fusion protein; and
  (ii) all or part of an antigenic protein as C-terminal moiety of the fusion protein.

CD134L is a type II transmembrane belonging to the TNF receptor family. The protein consists of a short N terminal cytosolic tail and a large C terminal extracellular domain. It is expressed on the cell surface as a trimer, preferentially on activated B cells (Miura et al., *Mol Cell Biol* 11, 1313-1325 (1991); Croft, M., *Annu Rev Immunol* 28, 57-78 (2010)). According to the present invention this type II transmembrane protein is suitable as carrier for cell surface expression of antigens fused to its carboxyterminal end (FIG. 1). The fusion protein is expressed and the antigenic protein which is fused to the carboxyterminal end of CD134L is expressed on the cell surface. Therefore, the construct is suitable for the production of antibodies. Any CD134L, a fragment or homologous protein thereof is suitable as N-terminal carrier moiety as long as the function is as for example that of human CD134L. CD134L proteins and their homologues are found in diverse animal species such as vertebrate, fish (including agnatha, chondrichthyes, osteichthyes), amphibian, reptile, avian or mammalian animal species. In a preferred embodiment of the expression vector said CD134L is mammalian CD134L. In a further preferred embodiment said CD134L is human CD134L. In yet another preferred embodiment said CD134L is rodent CD134L.

In a further preferred embodiment, the CD134L comprises or consists of a amino acid sequence shown in SEQ ID NO: 2.

In an embodiment, the fragment of CD134L is a biologically active fragment of CD134L and comprises the cytosolic and transmembrane domain, preferably the fragment of CD134L—used in the above described fusion protein as "CD134L moiety"—is a polypeptide having at least the amino acid sequence from amino acid position 1 to 50 of SEQ ID NO: 2, preferably at least from amino acid position 1 to 60 of SEQ ID NO: 2, further preferred at least from amino acid position 1 to 80, even further preferred at least from amino acid position 1 to 100, more preferred at least from amino acid position 1 to 120, still further preferred at least from amino acid position 1 to 140 and most preferred at least from amino acid position 1 to 160 of the amino acid sequence shown in SEQ ID NO: 2.

In one embodiment, the nucleic acid sequence coding for the CD134L-moiety is selected from:
(a) a polynucleotide encoding a protein having the amino acid sequence shown in SEQ ID NO: 2;
(b) a polynucleotide encoding a protein which protein has at least 60% identity to the amino acid sequence of the protein of (a);
(c) a polynucleotide encoding a protein having an amino acid sequence comprising a deletion, substitution, insertion and/or addition of one to 75 amino acid residues with respect to the amino acid sequence shown in SEQ ID NO: 2;
(d) a polynucleotide having a nucleotide sequence shown in SEQ ID NO: 1;
(e) a polynucleotide hybridizing under the stringent conditions comprising a wash in a solution of 1× sodium chloride/sodium citrate (SSC) and 0.1% sodium dodecyl sulfate (SDS) at 65° C. to the full complement of the polynucleotide having a nucleotide sequence shown in SEQ ID NO: 1.

In a further embodiment, the antigenic protein as C-terminal moiety of the fusion protein, which fused to the CD134L moiety, is 10 to 1000, 10 to 500, 10 to 400, 10 to 300, 10 to 200, 10 to 150, 10 to 100, 10 to 80, 10 to 60, 10 to 50, 10 to 40, 10 to 30, 10 to 20, 5 to 15 and 5 to 10 amino acid residues in length. In another embodiment, the antigenic protein is having a length of at least 20, 30, 50, 80, 100, 150, 200, 300, 400, 500, 600, 700, 800 amino acid residues in length, or preferably 20 to 1000, 20 to 500, 30 to 500, 50 to 500, 80 to 500, 100 to 500, 150 to 500, 200 to 500, 300 to 500, 400 to 500, 500 to 1000, 600 to 1000, 800 to 1000 and 900 to 1000 amino acid residues in length.

In another embodiment of the expression vector, the promoter may be any one of SV40 early and late promoters, CMV promoter (immediate-early promoter-regulatory region of human cytomegalovirus) and promoters of retroviral LTRs, such as those of the Rous sarcoma virus ("RSV"), metallothionein promoters, such as the mouse metallothionein-I promoter.

Further, the expression vector may comprise a sequence coding for a linker peptide interposed between (i) and (ii). This means that the fusion protein comprises an amino acid sequence wherein CD134L, a fragment or homologous protein thereof as N-terminal moiety is connected to the antigenic protein (C-terminal moiety) by a linker peptide. Such linker peptide preferably is $(G_4S)_3$ (SEQ ID NO: 31). In alternative embodiments, a linker peptide is not present.

In one embodiment, a recombinant cell, transformed or transfected with the expression vector as described above is provided. Preferably, the recombinant cell is a eukaryotic cell.

Also provided is a method for producing an antibody specific for an antigen comprising administering the expression vector of claim 1 to a subject animal, wherein said expression vector comprises a gene in operable linkage with a promoter, which gene encodes upon expressing a fusion protein comprising (i) CD134L, a fragment or homologous protein thereof as N-terminal moiety of the fusion protein, and (ii) all or part of an antigenic protein as C-terminal moiety of the fusion protein, and said antibody is generated in the subject animal.

In one embodiment, the method comprises a step of administering the expression vector via electroporation. In this preferred embodiment the expression vector is administered "as is" to a subject animal, also referred to as "naked" DNA or expression vector. According to this method of administering said expression vector via electroporation said expression vector is administered into the subject animal by DNA electrotransfer, which method comprises the steps of intramuscular injection of the DNA and applying electric pulses to the skin of the subject animal close to the injection site.

In an alternative embodiment, the expression vector is administered to a subject animal after transformation or transfection into a cell capable of a expressing the fusion protein on its surface.

Accordingly, the method may comprise a step of administering the recombinant cell transformed or transfected with the expression vector of the present invention as described above to a subject animal, wherein said expression vector produces a fusion protein of (i) and (ii) on the surface of said recombinant cell, under conditions favoring the generation of antibodies specific to (ii) by said subject animals.

In one embodiment, the antigenic protein is autologous to the subject animal. In particular, the antigenic protein is autologous to the subject animal and the CD134L protein is foreign to the subject animal. The antigenic protein can be any protein including proteins for the subject animal because it may be possible to induce an antibody response against self-antigens, and therefore breaking natural tolerance.

In a further embodiment, the method may comprise recovering the generated antibody from the serum of the subject animal.

In yet another embodiment, the method may comprise the following steps:
(i) recovering cells from the spleen of the subject-animal which produce the antibody;
(ii) immortalizing the cells to generate hybridoma cell producing the antibody;
(iii) culturing the hybridoma cell in a medium wherein the antibody accumulates in the medium; and
(iv) recovering monoclonal antibodies from the culture medium.

In another embodiment, an expression vector for generating an antibody directed to an antigen is provided. The expression vector may comprise a polynucleotide in operable linkage with a promoter, wherein the polynucleotide encodes a fusion protein comprising:
(i) a polypeptide having at least 35% amino acid identity to the polypeptide of SEQ ID NO:2 which anchors in a cell membrane as the N-terminal moiety of the fusion protein; and
(ii) an antigenic protein or an antigenic fragment thereof as the C-terminal moiety of the fusion protein.

In some embodiments, the N-terminal moiety of the fusion protein in the expression vector comprises the polypeptide of SEQ ID NO: 26 or a polypeptide having at least 95% amino acid sequence identity to the polypeptide of SEQ ID NO. 26 which anchors in a cell membrane.

In some other embodiments, the N-terminal moiety of the fusion protein in the expression vector comprises the polypeptide of SEQ ID NO: 27 or a polypeptide having at least 95% amino acid sequence identity to the polypeptide of SEQ ID NO. 27 which anchors in a cell membrane.

In still some other embodiments, the N-terminal moiety of the fusion protein in the expression vector comprises the polypeptide of SEQ ID NO: 28 or a polypeptide having at least 95% amino acid sequence identity to the polypeptide of SEQ ID NO. 28 which anchors in a cell membrane.

In still some other embodiments, the N-terminal moiety of the fusion protein in the expression vector comprises the polypeptide of SEQ ID NO: 29 or a polypeptide having at least 95% amino acid sequence identity to the polypeptide of SEQ ID NO. 29 which anchors in a cell membrane.

In another embodiment, the expression vector further comprises a linker peptide interposed between (i) and (ii).

In still another embodiment, the linker peptide comprises $(G_4S)_3$ (SEQ ID NO: 31).

In some other embodiments, an expression vector for generating an antibody directed to an antigen is provided. The expression vector may comprise a polynucleotide encoding a fusion protein comprising an antigenic protein or an antigenic fragment thereof in operable linkage with a promoter, wherein said polynucleotide encoding said fusion protein comprises a nucleic acid sequence encoding said antigenic protein or said antigenic fragment thereof as a C-terminal moiety of said fusion protein and a nucleic acid sequence encoding a polypeptide which anchors in the cell membrane as an N-terminal moiety of said fusion protein, wherein said nucleic acid sequence encoding the polypeptide which anchors in the cell membrane comprises a nucleic acid sequence selected from the group consisting of:

a polynucleotide having at least 50% nucleic acid identity to the polynucleotide of SEQ ID NO:1, wherein said polynucleotide encodes a polypeptide which anchors in the cell membrane.

In some embodiments, the polynucleotide having at least 50% nucleic acid identity to the polynucleotide of SEQ ID NO:1 in the expression vector comprises the polynucleotide of SEQ ID NO: 22 or a polynucleotide having at least 95% nucleic acid sequence identity to the polynucleotide of SEQ ID NO. 22 which encodes a polypeptide which anchors in the cell membrane.

In some other embodiments, the polynucleotide having at least 50% nucleic acid identity to the polynucleotide of SEQ ID NO:1 in the expression vector comprises the polynucleotide of SEQ ID NO: 23 or a polynucleotide having at least 95% nucleic acid sequence identity to the polynucleotide of SEQ ID NO. 23 which encodes a polypeptide which anchors in the cell membrane.

In still some other embodiments, the polynucleotide having at least 50% nucleic acid identity to the polynucleotide of SEQ ID NO:1 in the expression vector comprises the polynucleotide of SEQ ID NO: 24 or a polynucleotide having at least 95% nucleic acid sequence identity to the polynucleotide of SEQ ID NO. 24 which encodes a polypeptide which anchors in the cell membrane.

In still some other embodiments, the polynucleotide having at least 50% nucleic acid identity to the polynucleotide of SEQ ID NO:1 in the expression vector comprises the polynucleotide of SEQ ID NO: 25 or a polynucleotide having at least 95% nucleic acid sequence identity to the polynucleotide of SEQ ID NO. 25 which encodes a polypeptide which anchors in the cell membrane.

In other embodiments, the expression vector further comprises a nucleic acid sequence encoding a linker peptide interposed between the nucleic acid sequence encoding said antigenic protein or antigenic fragment thereof and the nucleic acid sequence encoding said polypeptide which anchors in the cell membrane.

In some other embodiments, the linker peptide present in the expression vector is $(G_4S)_3$ (SEQ ID NO: 31).

In still some other embodiments, the promoter is selected from the group consisting of SV40 early and late promoters, CMV promoter and promoters of retroviral LTRs, promoter of Rous sarcoma virus ("RSV"), metallothionein promoters, and mouse metallothionein-I promoter.

In another embodiment, a recombinant cell, transformed or transfected with an expression vector according to any of the embodiments discussed above is provided.

In some embodiments, the recombinant cell is a eukaryotic cell.

In still another embodiment, an expression vector for generating an antibody directed to an antigen in a subject animal is provided. The expression vector may comprise a polynucleotide in operable linkage with a promoter, wherein the polynucleotide encodes a fusion protein comprising:
  (i) a CD134L polypeptide that is orthologous to human CD134L or a polypeptide having at least 95% amino acid identity to a CD134L polypeptide that is orthologous to human CD134L which anchors in a cell membrane as the N-terminal moiety of the fusion protein; and
  (ii) an antigenic protein or an antigenic fragment thereof as the C-terminal moiety of the fusion protein.

In some embodiments, the polypeptide of CD134L that is orthologous to human CD134L or said polypeptide having at least 95% amino acid identity to a CD134L polypeptide that is orthologous to human CD134L which anchors in a cell membrane is from a species different from the species of the subject animal.

In some other embodiments, the N-terminal moiety of the fusion protein comprises the polypeptide of SEQ ID NO: 26 or a polypeptide having at least 95% amino acid sequence identity to the polypeptide of SEQ ID NO. 26 which anchors in a cell membrane.

In still some other embodiments, the N-terminal moiety of the fusion protein comprises the polypeptide of SEQ ID NO: 27 or a polypeptide having at least 95% amino acid sequence identity to the polypeptide of SEQ ID NO. 27 which anchors in a cell membrane.

In still some other embodiments, the N-terminal moiety of the fusion protein comprises the polypeptide of SEQ ID NO: 28 or a polypeptide having at least 95% amino acid sequence identity to the polypeptide of SEQ ID NO. 28 which anchors in a cell membrane.

In still some other embodiments, the N-terminal moiety of the fusion protein comprises the polypeptide of SEQ ID NO: 29 or a polypeptide having at least 95% amino acid sequence identity to the polypeptide of SEQ ID NO. 29 which anchors in a cell membrane.

In certain embodiments, the expression vector further comprises a linker peptide interposed between (i) and (ii).

In some embodiments, the linker peptide present in the expression vector is $(G_4S)_3$ (SEQ ID NO: 31).

In some other embodiments, the subject animal applicable in any embodiments of the invention is a human.

In another embodiment, an expression vector for generating an antibody directed to an antigen is provided. The expression vector may comprise a polynucleotide in operable linkage with a promoter, wherein the polynucleotide encodes a fusion protein comprising:
  (i) a CD134L polypeptide or a fragment thereof as the N-terminal moiety of the fusion protein, wherein said CD134L polypeptide or fragment thereof anchors in the cell membrane; and
  (ii) an antigenic protein or an antigenic fragment thereof as the C-terminal moiety of the fusion protein.

In some embodiments, the fragment of the CD134L polypeptide comprises the amino acid sequence from amino acid positions 24 to 50 of the polypeptide of SEQ ID NO. 2 or a polypeptide having at least 95% amino acid sequence identity to the amino acid sequence from amino acid positions 24 to 50 of the polypeptide of SEQ ID NO. 2.

In some other embodiments, the fragment of the CD134L polypeptide comprises the amino acid sequence from amino acid positions 24 to 50 of the polypeptide of SEQ ID NO. 2 or a polypeptide having at least 80% amino acid sequence identity to the amino acid sequence from amino acid positions 24 to 50 of the polypeptide of SEQ ID NO. 2.

In still some other embodiments, the fragment of the CD134L polypeptide comprises the amino acid sequence from amino acid positions 24 to 50 of the polypeptide of SEQ ID NO. 2 or a polypeptide having at least 70% amino acid sequence identity to the amino acid sequence from amino acid positions 24 to 50 of the polypeptide of SEQ ID NO. 2.

In still some other embodiments, the fragment of the CD134L polypeptide comprises the amino acid sequence from amino acid positions 24 to 50 of the polypeptide of SEQ ID NO. 2 or a polypeptide having at least 50% amino acid sequence identity to the amino acid sequence from amino acid positions 24 to 50 of the polypeptide of SEQ ID NO. 2.

In still some other embodiments, the fragment of the CD134L polypeptide comprises an amino acid sequence selected from the group consisting of the amino acid sequence from amino acid positions 24 to 50 or 23-46 of the polypeptide of SEQ ID NO. 26, the amino acid sequence from amino acid positions 26 to 53 or 25-49 of the polypeptide of SEQ ID NO. 27, the amino acid sequence from amino acid positions 24 to 50 or 23-46 of the polypeptide of SEQ ID NO. 28, the amino acid sequence from amino acid positions 26 to 53 or 25-48 of the polypeptide of SEQ ID NO. 29 and a polypeptide having at least 95% amino acid sequence identity to any of the foregoing polypeptides.

BRIEF DESCRIPTION OF THE FIGURES

FIG. 1 shows the expression of antigens as cell surface type II membrane fusion proteins. Panel A is a schematic representation of the pCD1-CD134L vector constructed in order to express antigens fused to the carboxyterminal end of human CD134L. Panel B is a schematic representation of transgene expression as a trimeric cell surface protein.

FIG. 6 shows an alignment result of various orthologous CD134L protein sequences. The amino acid residues are underlined when at least three corresponding amino acids over the five different sequences are identical.

FIG. 7 shows an alignment result of various orthologous CD134L nucleotide sequences. The nucleic acid residues are underlined when at least three corresponding amino acids out of the five different sequences are identical. The figure (at the bottom thereof) also presents a table summarizing the % identities between various CD134L nucleotide sequences and the reference sequence, the human CD134L nucleotide sequence.

FIGS. 9A to 9J show FACS analysis results of CD134L presentation exemplified with various CD134L sequences. FIGS. 9B, 9D, 9F, 9H, and 9J show examples of the results obtained with the platypus CD134L sequence, the human CD134L sequence, the mouse CD134L sequence, the rabbit CD134L sequence, and the alpaca CD134L sequence, respectively. As a negative control, unspecific sera was used (FIGS. 9A, 9C, 9E, 9G, and 9I).

FIG. 10A shows the results obtained from staining done on untransfected NIH3T3 cells (i.e. a negative control) and FIGS. 10B and 10C show the results from staining on NIH3T3 cells transfected with the expression vectors expressing either *Mus musculus* CD134L sequence or the *Oryctolagus cuniculus* CD134L sequence, with the antigen and linker sequence of (GGGGS)₃ (SEQ ID NO: 31).

FIG. 11A shows the result from the staining done on untransfected NIH3T3 cells (i.e. a negative control) and FIGS. 11B and 11C show the results from the staining on NIH3T3 cells transfected with the expression vectors expressing either the *Mus musculus* CD134L sequence or *Ornithorhynchus anatinus* CD134L sequence, fused to the antigen and having a linker sequence of (GGGGS)₃ (SEQ ID NO: 31) disposed between the CD134L sequence and the antigen. The antigen is a 244 amino acid part of an antibiotic-resistance protein isolated from bacteria (Enterobacteriaceae).

FIG. 12A shows the result from staining done on untrasfected CHO cells (i.e. a negative control) and FIGS. 12B and 12C show the results from staining on CHO cells transfected with the expression vectors expressing either the *Ornithorhynchus anatinus* CD134L sequence or the *Vicugna pacos* CD134L sequence, fused to the antigen and having the linker sequence of GGGGS (SEQ ID NO: 30) disposed between the CD134L sequence and the antigen. The antigen is a 307 amino acid part of a human GCSF receptor protein.

FIG. 13 shows a sequence alignment of the *Ornithorhynchus anatinus* CD134L sequence and the *Vicugna pacos* CD134L sequence in which the identical amino acid residues are underlined.

FIG. 14 shows a sequence alignment with the CD134L from *Ornithorhynchus anatinus* as a reference sequence compared to the sequences of the CD134L proteins from *Vicugna pacos, homo sapiens, Oryctolagus cuniculus*, and *mus musculus*.

FIGS. 15A and 15B show FACS results obtained from CHO cells transfected with an expression vector expressing the *Ornithorhynchus anatinus* CD134L without an antigen (FIG. 15A), or expressing the *Ornithorhynchus anatinus* CD134L with an antigen. The antigen utilized in this experiment is 231 amino acids of a human proteoglycan.

FIGS. 16A, 16B, 16C, and 16D show FACS analysis results using different antigens presented by the same *Mus musculus* CD134L sequence. FIG. 16A shows the result from staining done on NIH3T3cells transfected with the expression vector which expressed no antigen (i.e. a negative control). In contrast, FIGS. 16B, 16C, and 16D show the results from staining on NIH3T3cells cells transfected with the expression vectors expressing the *Mus musculus* CD134L sequence, the linker sequence of (GGGGS)₃ (SEQ ID NO: 31), and either one of the following antigens: (1) an antigen 1 that is 66 amino acids from a human transmembrane protein (FIG. 16B); (2) an antigen 2 that is 174 amino acids from a human muscarinic receptor (FIG. 16C); and (3) an antigen 3 that is 135 amino acids of a human protein expressed by neuronal precursor cells (FIG. 16D).

FIG. 17A shows the result from staining done on untrasfected CHO cells (i.e. a negative control). FIGS. 17B and 17C show the results from staining with CHO cells transfected with expression vectors expressing the *Ornithorhynchus anatinus* CD134L sequence fused to the antigen, either with the linker sequence of (GGGGS)₃ (SEQ ID NO: 31) disposed between the CD134L sequence and the antigen (FIG. 17B) or without the linker (FIG. 17C).

DETAILED DESCRIPTION OF CERTAIN EMBODIMENTS

This invention relates to a method of generating antibodies. More particularly, the method involves administering an expression vector wherein a nucleic acid molecule encoding a cell surface type 2 transmembrane protein or a functional equivalent thereof is concatenated to a nucleic acid molecule encoding an antigen of interest, where the nucleic acid molecule encoding the antigen of interest is fused to the type 2 transmembrane protein or a functional equivalent thereof in the form of an expression vector in operable linkage with a promoter, can be administered as "naked DNA," or following transformation or transfection of a recipient cell, where the cell is administered.

Figure 2:
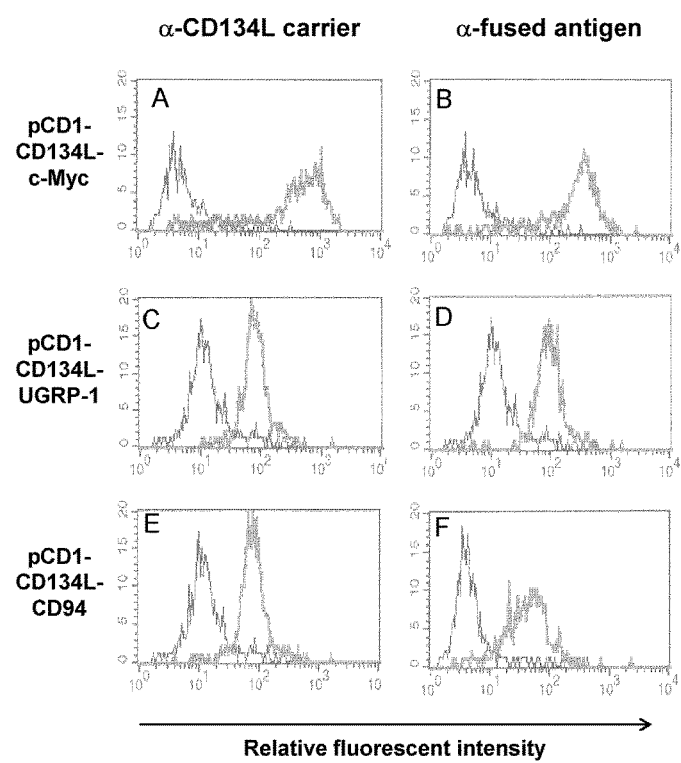
FIG. 2 shows the cell surface expression of antigens fused to the carboxyterminal end of CD134L. pCD1-CD134L derived vectors were constructed to express portion of c-Myc, UGRP-1 and CD94 antigens fused to CD134L (Table 1, AA cloned). IR983F cell lines stably expressing the fusion protein were produced. Untransfected cells (U) or transfected cells (T) were treated for cell surface indirect immunofluorescent staining of the CD134L carrier (Panels A, C, and E) or the staining of c-Myc, (Panel B), UGRP-1 (Panel D) or CD94 (Panel F) and then analysed by flow cytometry.

CD134L is a type II transmembrane belonging to the TNF receptor family. The protein consists of a short N terminal cytosolic tail and a large C terminal extracellular domain. It is expressed on cell surface as a trimer, preferentially on activated B cells (Miura et al., *Mol Cell Biol* 11, 1313-1325 (1991); Croft, M., *Annu Rev Immunol* 28, 57-78 (2010)). In some studies, the inventors tested whether this type II transmembrane protein could be used as carrier for cell surface expression of antigens fused to its carboxyterminal end. To test this hypothesis, a vector nicknamed pCD1-CD134L was constructed as described in detail in the examples (see FIG. 1). Next, epitopes derived from human c-Myc (here a peptide of 10 amino acid residues), UGRP-1 (here a polypeptide of 73 amino acid residues) and CD94 (here a polypeptide of 144 amino acid residues) were cloned in the pCD1-134L vector. IR983F cells were then stably transfected with the resulting vectors. Derived cell lines resistant to hygromycin were then stained for indirect immunofluorescent detection of cell surface expression of the CD134L and the fused antigens (FIG. 2). The results presented in FIG. 2 demonstrate that the fusion of antigens varying in length between 10 and 144 amino acid residues, and derived from different protein types, to the carboxyterminal end of the CD134L did not prevent its cell surface expression (FIG. 2, panels A, C and E). Immunofluorescent staining raised against the fused antigens confirmed their cell surface expression (FIG. 2, panels B, D and F).

The data presented demonstrate that fusion of antigens at the carboxyterminal end of the CD134L type II protein is an efficient method to induce their cell surface expression. In comparison to type I protein carriers, the type II CD134L carrier has the major advantage to allow the cloning of the antigen in frame of the carboxyterminal end; thereby avoiding any interference with the anchor signal located at the N terminal end. Next, the potential was tested of the pCD1-CD134L vector in an immunization scheme relying on the injection of histocompatible living cells stably expressing the antigen fused to the CD134L. The data presented below demonstrate that this method was used successfully to produce mouse antibodies raised against IRCAL (*Ixodes ricinus* calreticulin: Tick secreted protein) and rat monoclonal antibodies (Mabs) raised against a domain (40 amino acid residues in length) of Vaccinia Virus A56 (type I transmembrane protein).

Figure 3:
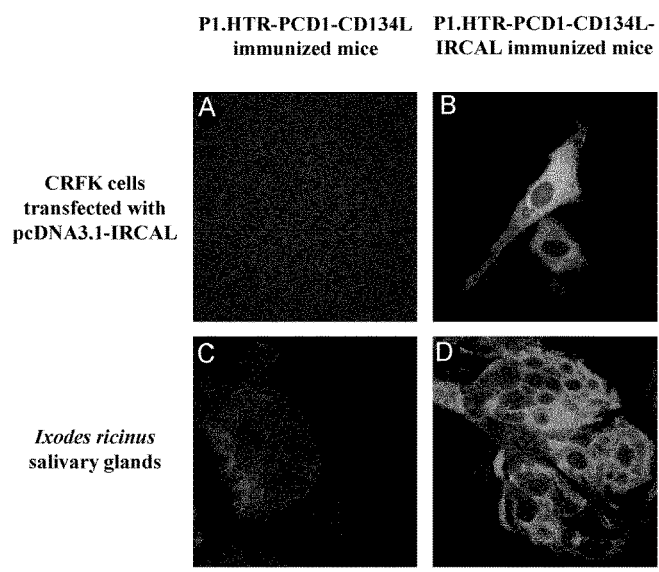
FIG. 3 shows the production of anti-IRCAL antibodies. Mice were immunized with live P1.HTR cell lines stably transfected with pCD1-CD134L or pCD1-CD134L-IRCAL. Sera were collected from the animals and used for indirect immunofluorescent staining of CRFK cells transfected with pcDNA3.1-IRCAL vector and *Ixodes ricinus* salivary glands. Cells were mounted and analysed by confocol microscopy. The side of panels A-B and C-D corresponds to 75 and 200 µm of the specimen, respectively.

For production of mouse antibodies raised against IRCAL, most of IRCAL ORF (amino acid residues 17-413) was cloned in the pCD1-CD134L vector. The resulting pCD1-CD134L-IRCAL plasmid was stably transfected in P1.HTR cells. Cell surface expression of the transgene was controlled by indirect immunofluorescent staining using the rat Mab LO-CD134L (data not shown). Mice were immunized by injection of stably transfected living cells as described in the examples. At the end of the immunization protocol, sera were collected and analysed for the presence of anti-IRCAL antibodies by indirect immunofluorescent staining of cells transiently expressing IRCAL (FIG. 3, panel B). All immunized mice (n=10) had detectable antibodies raised against IRAC with titre ranging from 1/512 up to 1/4096 (highest dilution leading to a positive signal). Finally, the ability of the antibodies produced was controlled to react against the native protein expressed in *Ixodes ricinus*. Tick salivary glands were treated for indirect immunofluorescent staining and analysed by confocal microscopy (FIG. 3, panel D). Confocal examination of the samples demonstrated that the antibodies produced recognised a protein abundantly expressed in the endoplamsic reticulum and secretary vesicles.

The immunisation method developed in the present study was also used to produce rat Mabs raised against a domain of Vaccinia virus A56 (AA 48-88). This domain is conserved amongst orthopoxviruses such as Variola virus (smallpox), monkeypox, cowpox and ectromelia. A IR983F cell line stably transfected with the pCD1-CD134L-A56 vector was produced and cell surface expression of the transgene was controlled by flow cytometry. Next, an histocompatible LOU-C rat was immunised with irradiated living cells. The serum collected from the rat at the end of the immunization protocol contained high titre (1/8192; highest dilution leading to a positive signal) of anti-Vaccinia virus antibodies as revealed by indirect immuofluorescent staining of viral plaques (data not shown). Rat spleen was used to produce Mabs. From a single fusion, the three step screening described in the methods led to the selection of 7 stable hybridomas secreting Mabs inducing a strong staining of VV infected cells. Among these Mabs, four were IgG2b, two were IgG1 and one was an IgG2a, demonstrating that the immunization procedure used induced isotype switching and probably antibody affinity maturation. The results obtained with one of them (Mab A56VV1) are presented in FIG. 4.

The property of the type II transmembrane CD134L to act as a carrier for cell surface expression of antigens fused to its carboxyterminal end has been demonstrated. This property was established for antigens between 10 up to 396 AA and derived from different protein types. The cell surface expression of CD134L as a trimer could consequently contribute to the immunogenicity of the CD134L-antigen fusion proteins observed in the present study.

In addition, variants of the CD134L moiety may also be used, which variants preferably have at least 20%, 25%, 30%, 35%, 40%, 45%, 50%, 55%, 60%, 65%, 70%, 75%, 80%, 85%, 90%, 95%, 96%, 97%, 98%, 99% or more identity to SEQ ID NO: 2.

Further, variants of the CD134L moiety may also be used, said variants being represented by a protein having an amino acid sequence comprising a deletion, substitution, insertion and/or addition of one to 75 more amino acids with respect to the amino acid sequence shown in in SEQ ID NO: 2. In a preferred embodiment 1 to 60, preferred 1 to 50, more preferred 1 to 40, further preferred 1 to 30, still further preferred 1 to 20, even further preferred 1 to 15, more preferred 1 to 10, further preferred 1 to 5, and most preferred 1, 2, 3 or 4 amino acids are deleted, substituted, inserted and/or added in respect to the sequence shown in SEQ ID NO: 2. The term "addition" means N-terminal or C-terminal addition of amino acid residues in respect to above mentioned sequences.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence.

Optimal alignment of sequences for aligning a comparison window may, for example, be conducted by the local homology algorithm of Smith and Waterman *Adv. Appl. Math.* 2:482 (1981), by the homology alignment algorithm of Needleman and Wunsch J. Mol. Biol. 48:443 (1970), by the search for similarity method of Pearson and Lipman Proc. Natl. Acad. Sci. U.S.A. 85:2444 (1988), or by computerized implementations of these algorithms (GAP, BEST-FIT, FASTA, and TFASTA in the Wisconsin Genetics Software Package Release 7.0, Genetics Computer Group, 575 Science Dr., Madison, Wis.).

As applied to polypeptides, the terms "substantial identity" or "substantial sequence identity" mean that two polypeptide sequences, when optimally aligned, such as by the programs GAP or BESTFIT using default gap weights, share at least 20%, 25%, 30%, 35%, 40%, 45%, 50%, 55%, 60%, 65%, 70%, 75%, 80%, 85%, 90%, 95%, 96%, 97%, 98%, 99% sequence identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

Functional Equivalents

The terms "functional equivalents" and "functional variants" are used interchangeably herein. Functional equivalents of CD134L encoding DNA are isolated DNA fragments that encode a polypeptide that exhibits a particular function of the CD134L, which may also be maintained in a fusion construct. A functional equivalent of a CD134L polypeptide is a polypeptide that is anchored in the cell membrane. Functional equivalents therefore also encompass biologically active fragments having the same or different sizes as a wild type, naturally occurring CD134L sequence.

Functional protein or polypeptide equivalents may contain only conservative or homologous substitutions of one or more amino acids in the amino acid sequences shown in SEQ ID NO: 2 or substitutions, insertions or deletions of non-essential amino acids. Accordingly, a non-essential amino acid is a residue that can be altered in an amino acid sequence shown in SEQ ID NO: 2 without substantially altering the biological function. For example, amino acid residues that are conserved among the CD134L proteins found in several different species are predicted to be particularly unamenable to alteration. Furthermore, amino acids conserved among the CD134L proteins and other CD134L are not likely to be amenable to alteration.

The term "conservative substitution" or substitution by "homologous" amino acid residues is intended to mean that a substitution in which the amino acid residue is replaced with an amino acid residue having a similar side chain. These families are known in the art and include amino acids with basic side chains (e.g. lysine, arginine and hystidine), acidic side chains (e.g. aspartic acid, glutamic acid), uncharged polar side chains (e.g., glycine, asparagines, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine tryptophan, histidine).

Conservative amino acid substitutions usually have minimal impact on the activity of the resultant protein. Such substitutions are described below. Conservative substitutions replace one amino acid with another amino acid that is similar in size, hydrophobicity, charge, polarity, steric features, aromaticity etc. Such substitutions generally are conservative when it is desired to finely modulate the characteristics of the protein.

"Homologous" amino acid residues as used herein refer to amino acid residues which have similar chemical properties concerning hydrophobicity, charge, polarity, steric features, aromatic feature etc. Examples for amino acids which are homologous to each other include in terms of positive charge lysine, arginine, histidine; in terms of negative charge: glutamic acid, aspartic acid; in terms of hydrophobicity: glycine, alanine, valine, leucine, isoleucine, proline, phenylalanine; in terms of polarity serine, threonine, cysteine, methionine, tryptophan, tyrosine, asparagine, glutamine; in terms of aromaticity: phenylalanine, tyrosine, tryptophan; in terms of chemically similar side groups: serine and threonine; or glutamine and asparagines; or leucine and isoleucine. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

"Orthologous" sequences (of nucleic acids as well as polypeptides) as used herein refer to homologous sequences where a sequence is found in at least two different species. The identity or homology between the orthologues sequences (of nucleic acid as well as amino acid) often vary significantly, ranging from about 20% to 100%. For example, the sequences orthologues to the human CD134 sequence (of nucleic acids as well as polypeptides) can be found in many other different species including, but not limited to, *Oryctolagus cuniculus* (rabbit), *Mus musculus* (mouse), *Vicugna pacos* (alpaca), and *Ornithorhynchus anatinus* (platypus). FIG. 6 shows the alignment of some selected CD134L amino acid sequences that are orthologous to the human CD134L sequence. The amino acid sequence identity of the orthologous CD134L sequences to the human CD134L sequence shown in FIG. 6 ranges from about 35% to 66%. Functional nucleic acid equivalents may typically contain silent mutations or mutations that do not alter the biological function of encoded polypeptide. Accordingly, the invention provides, at least in some embodiments, nucleic acid molecules encoding a fusion protein comprising a CD134L moiety that contain changes in amino acid residues that are not essential for a particular biological activity. In other embodiments, nucleic acid molecules encoding a fusion protein comprising a CD134L moiety that is orthologous to the human CD134L moiety. Such proteins differ in the amino acid sequence shown in SEQ ID NO: 2 yet they retain the biological activity as defined herein. In one embodiment the isolated nucleic acid molecule comprises a nucleotide sequence encoding a protein, wherein the protein has a percent identity of at least about 20%, 25%, 30%, 35%, 40%, 45%, 50%, 55%, 60%, 65%, 70%, 75%, 80%, 85%, 90%, 95%, 96%, 97%, 98%, 99% or more to the amino acid sequence shown in of SEQ ID NO: 2.

Exemplary nucleic acid molecules encoding protein sequences that are functionally equivalent to the amino acid sequence of SEQ ID NO:2 include, but are not limited to, the nucleic acid sequences of SEQ ID NOs: 26-29, and homologues sequences thereto. The sequences homologous to any of the nucleic acid sequences of SEQ ID NOs: 1 and 22-25 have at least about 20%, 25%, 30%, 35%, 40%, 45%, 50%, 55%, 60%, 65%, 70%, 75%, 80%, 85%, 90%, 95%, 96%, 97%, 98%, 99% or more sequence identity to at least one of the nucleic acid sequences of SEQ ID NOs: 1 and 22-25.

Some of proteins that are functionally equivalent to the amino acid sequence of SEQ ID NO: 2 include, but not limited to, the amino acid sequences of SEQ ID NOs: 26-29, and homologues sequences thereof. In some embodiments, the functional equivalents of the human CD134L protein sequence include different CD134L sequences having the amino acid sequence identity of at least 30% to the human CD134L sequence. In some embodiments, the amino acid identity present in the functional equivalents of the human CD134L protein sequence is at least about 20%, 25%, 30%, 35%, 40%, 45%, 50%, 55%, 60%, 65%, 70%, and any intervening number of amino acid identity to the human CD134L protein sequence.

For example, guidance concerning how to make phenotypically silent amino acid substitutions is provided in Bowie, J. U. et al., Science 247:1306-1310 (1990) wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As the authors state, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, supra, and the references cited therein. In addition to the foregoing, at least in some embodiments, the amino acid residues or sequences retained in functional CD134L equivalents (or derivatives) can be deduced from the alignment of homologous or orthologous sequences of CD134L. For example, FIG. 6 illustrates the alignment of some CD134L orthologous sequences and reveals individual amino acids that are conserved (to different extents in some positions) in at least some species. Functional equivalents may have amino acid substitutions relative to the human CD134L protein in one or more of the amino acid residues that are conserved in at least two, three, four, five or more different species.

An isolated nucleic acid molecule encoding a protein that is homologous or functionally equivalent to the protein shown in SEQ ID NO: 2 can be created by introducing one or more nucleotide substitutions, additions or deletions into the coding nucleotide sequences such that one or more amino acid substitutions, deletions or insertions are introduced into the encoded protein. Such mutations may be introduced by standard techniques, such as site-directed mutagenesis and PCR-mediated mutagenesis. Analysis of the human CD134L protein sequence of SEQ ID NO: 2, as an example, using software and information from the Uniprot database indicates that that the amino acid sequence from amino acid position 1 to 23 is likely to be cytoplasmic and the amino acid sequence from amino acid position 51 to 183 is likely to be extracellular. In addition, the analysis indicates that the amino acid sequence from amino acid position 24 (Leu) to 50 (Leu) of SEQ ID NO: 2, and, within this area, amino acids 23 (Lys) to 46 (His) are likely to be involved in membrane anchoring. The corresponding regions of the orthologous CD134L proteins provided herein are also likely to be involved in membrane anchoring. Within SEQ ID NO: 2 amino acids from position 25 (Leu), position 26 (Leu), position 27 (Val), position 29 (Ser), position 35 (Gly), position 37 (Leu), position 39 (Cys), position 42 (Tyr), and position 44 (Cys) appear as the most conserved amino acids throughout different species (see FIG. 6) and therefore are likely to be important for the function of membrane anchoring. Similarly, the corresponding amino acid positions within the orthologous CD134L proteins provided herein are also likely to be important for the function of membrane anchoring. Accordingly, in some embodiments, a functionally equivalent protein sequence of CD134L or fragment thereof may comprise a polypeptide comprising the sequence of amino acids 24 to 50 or 23-46 of SEQ ID NO: 2 or a polypeptide having at least about 50%, 55%, 60%, 65%, 70%, 75%, 80%, 85%, 90%, 95%, 96%, 97%, 98%, or 99% amino acid sequence identity to the polypeptide of amino acid positions 24 to 50 or 23-46 of SEQ ID NO: 2. In some embodiments, the functionally equivalent protein sequence of CD134L or fragment thereof may comprise the polypeptide of amino acid positions 24 to 50 or 23-46 of SEQ ID NO: 26, the polypeptide of amino acid positions 26 to 53 or 25-49 of SEQ ID NO: 27, the polypeptide of amino acid positions 24 to 50 or 23-46 of SEQ ID NO: 28, or the polypeptide of amino acid positions 26 to 53 or 25-48 of SEQ ID NO: 29, or a polypeptide having at least about 50%, 55%, 60%, 65%, 70%, 75%, 80%, 85%, 90%, 95%, 96%, 97%, 98%, or 99% amino acid sequence identity thereto. In some embodiments, the functionally equivalent protein sequence of CD134L or fragment thereof may comprise one or more of the following conserved amino acids: Leu at the position corresponding to the Leu at position 25 of SEQ ID NO: 2, Leu at the position corresponding to the Leu at position 26 of SEQ ID NO: 2, Val at the position corresponding to the Val at position 27 of SEQ ID NO: 2, Ser at the position corresponding to the Ser at position 29 of SEQ ID NO: 2, Gly at the position corresponding to the Gly at position 35 of SEQ ID NO: 2, Leu at the position corresponding to the Leu at position 37 of SEQ ID NO:2, Cys at the position corresponding to the Cys at position 39 of SEQ ID NO: 2, Tyr ar the position corresponding to the Tyr at position 42 of SEQ ID NO: 2 or Cys at the position corresponding to the Cys at position 44 of SEQ ID NO: 2.

As defined herein, the term "substantially homologous" refers to a first amino acid or nucleotide sequence which contains a sufficient or minimum number of identical or equivalent (e.g., with similar side chain) amino acids or nucleotides to a second amino acid or nucleotide sequence such that the first and the second amino acid or nucleotide sequences have a common domain. For example, amino acid or nucleotide sequences which contain a common domain or full length sequence having at least about 20%, 25%, 30%, 35%, 40%, 45%, 50%, 55%, 60%, 65%, 70%, 75%, 80%, 85%, 90%, 95%, 96%, 97%, 98%, 99% or more of sequence identity to a reference sequence, such as a reference sequence selected from the group consisting of SEQ ID NOs: 1, 2, and 22-29 or a domain therein, are defined herein as having substantially homologous common domains or full length sequences respectively. In some embodiments, the domain may be a membrane anchoring domain or a nucleotide sequence encoding a membrane anchoring domain. For example, amino acid or nucleotide sequences which contain or encode a common domain, such as a membrane anchoring domain, for example, having about 60%, preferably 65%, more preferably 70%, even more preferably 75%, 80%, 85%, 90%, 95%, 96%, 97%, 98% or 99% identity or more to a common domain within or encoded by a reference sequence selected from the group consisting of SEQ ID NOs: 1, 2, and 22-29 are defined herein as sufficiently identical. In some embodiments, the membrane anchoring domain may comprise a polypeptide comprising the sequence of amino acids 24 to 50 or 23-46 of SEQ ID NO: 2 or a polypeptide having at least about 50%, 55%, 60%, 65%, 70%, 75%, 80%, 85%, 90%, 95%, 96%, 97%, 98%, or 99% amino acid sequence identity to the polypeptide of amino acid positions 24 to 50 or 23-46 of SEQ ID NO: 2. In some embodiments, the membrane anchoring domain may comprise the polypeptide of amino acid positions 24 to 50 or 23-46 of SEQ ID NO: 26, the polypeptide of amino acid positions 26 to 53 or 25-49 of SEQ ID NO: 27, the polypeptide of amino acid positions 24 to 50 or 23-46 of SEQ ID NO: 28, or the polypeptide of amino acid positions 26 to 53 or 25-48 of SEQ ID NO: 29, or a polypeptide having at least about 50%, 55%, 60%, 65%, 70%, 75%, 80%, 85%, 90%, 95%, 96%, 97%, 98%, or 99% amino acid sequence identity thereto. In some embodiments, the membrane anchoring domain may comprise one or more of the following conserved amino acids: Leu at the position corresponding to the Leu at position 25 of SEQ ID NO: 2, Leu at the position corresponding to the Leu at position 26 of SEQ ID NO: 2, Val at the position corresponding to the Val at position 27 of SEQ ID NO: 2, Ser at the position corresponding to the Ser at position 29 of SEQ ID NO: 2, Gly at the position corresponding to the Gly at position 35 of SEQ ID NO: 2, Leu at the position corresponding to the Leu at position 37 of SEQ ID NO:2, Cys at the position corresponding to the Cys at position 39 of SEQ ID NO: 2, Tyr ar the position corresponding to the Tyr at position 42 of SEQ ID NO: 2 or Cys at the position corresponding to the Cys at position 44 of SEQ ID NO: 2.

In some embodiments, "substantially homologous" amino acid or nucleotide sequences refer to amino acid or nucleotide sequences which contain or encode a sufficient or minimum number of identical or conserved amino acid residues relative to one another such that the substantially homologous amino acid or nucleotide sequences have one or more common domains. In some embodiments, the common domain may be a membrane anchoring domain of a CD134L protein as described above. In some embodiments, the substantially homologous amino acid or nucleotide sequences contain or encode a common domain having at least about 20%, 25%, 30%, 35%, 40%, 45%, 50%, 55%, 60%, 65%, 70%, 75%, 80%, 85%, 90%, 95%, 96%, 97%, 98%, 99% or more of sequence identity to a membrane anchoring domain of a CD134L protein as described above.

Also, nucleic acids encoding other CD134L family members including those are homologous, orthologous or functionally equivalent to the human CD134L sequence, which thus have a nucleotide sequence that differs from one or more nucleotide sequence disclosed herein can be used for constructing a fusion construct. Such nucleic acid molecules corresponding to variants (e.g. natural allelic variants) and homologues of the DNA can be isolated based on their homology to the nucleic acids disclosed herein using the cDNAs disclosed herein or a suitable fragment thereof, as a hybridisation probe according to standard hybridisation techniques preferably under highly stringent hybridisation conditions.

The term "functional equivalents" also encompasses the orthologues of the CD134L protein used herein. For example, the orthologues of the human CD134L protein are proteins that can be isolated from other species and possess a similar or identical biological activity to the human CD134L sequence. For example, the orthologues of the human CD134L protein may anchor in the membrane and have the ability to present an antigen fused thereto such that an immune response is generated against the antigen. Such orthologues can readily be identified as comprising an amino acid sequence that is substantially homologous to the amino acid sequences shown in SEQ ID NO: 2. Some the examples of such orthologous sequences include, but are not limited to, the amino acid sequences of SEQ ID NOs: 26-29.

In addition to naturally occurring allelic variants of the sequences provided herein, the skilled person will recognise that further changes can be introduced by mutation into the nucleotide sequences encoding the CD134 moiety thereby leading to changes in the amino acid sequence of the CD134L protein without substantially altering the function of the protein.

In a further embodiment, the CD134L has an amino acid sequence encoded by an isolated nucleic acid fragment capable of hybridising to a nucleic acid, preferably under highly stringent hybridisation conditions. Accordingly, in some embodiments, the protein is encoded by a nucleic acid sequence having at least about 20%, 25%, 30%, 35%, 40%, 45%, 50%, 55%, 60%, 65%, 70%, 75%, 80%, 85%, 90%, 95%, 96%, 97%, 98%, 99% or more sequence identity to the nucleic acid sequence shown in SEQ ID NO: 1 or one of SEQ ID NOs: 22-25. In some embodiments, the CD134L protein has an amino acid sequence having at least about 20%, 25%, 30%, 35%, 40%, 45%, 50%, 55%, 60%, 65%, 70%, 75%, 80%, 85%, 90%, 95%, 96%, 97%, 98%, 99% or more sequence identity to the amino acid sequence of SEQ ID NO: 2 or one of of SEQ ID NOs: 26-29.

Protein Fragments

In some embodiments, the invention makes use of CD134L fusion protein for generating antibodies. The CD134L moiety may include biologically active variants or fragments thereof.

Biologically active variants or fragments of a polypeptide of the invention include polypeptides comprising amino acid sequences substantially homologous or sufficiently identical to or derived from the amino acid sequence of the CD134L (e.g., the amino acid sequences shown in SEQ ID NO: 2 and SEQ ID NOs: 26-29), which can include fewer or more amino acids than the wild type full length protein, and exhibit at least one biological activity of the corresponding full-length protein, namely that the protein is properly anchored in the cell membrane. In a preferred embodiment, a fusion protein comprises at least one biologically active fragment of a CD134L according to the invention. A biologically active fragment of CD134L may comprise the cytosolic and transmembrane domain, preferably a polypeptide having at least the amino acid sequence from amino acid position 1 to 50 of SEQ ID NO: 2 or SEQ ID NOs: 26-29, or preferably at least from amino acid position 1 to 60 of SEQ ID NO: 2 or SEQ ID NOs: 26-29. A biologically active fragment may also comprise a membrane anchoring domain of a CD134L protein as described above. Within the fusion protein, the term "operatively linked" is intended to indicate that the CD134L and the non-CD134L polypeptide are fused in-frame to each other to the C-terminus of the CD134L. The non-CD134L polypeptide serves as antigenic protein, for raising antibodies directed to said antigenic protein.

The invention also makes use of nucleic acid fragments that encode the above biologically active fragments of the CD134L.

Fusion Proteins

CD134L, or a biologically active portion thereof, can be operatively linked to a non-CD134L polypeptide (e.g., heterologous amino acid sequences) to form fusion proteins. As used herein, a CD134L "chimeric protein" or "fusion protein" comprises a CD134L polypeptide or a functional equivalent thereof operatively linked to a non-CD134L polypeptide. In some embodiments, the chimeric protein or fusion protein may comprise a CD134L membrane anchoring domain operatively linked to a non-CD134L polypeptide.

A chimeric or fusion protein may be produced by standard recombinant DNA techniques. For example, DNA fragments coding for the different polypeptide sequences are ligated together in-frame in accordance with conventional techniques, for example by employing blunt-ended or staggerended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992).

Polynucleotides

In one embodiment, an expression vector comprising a gene encoding a fusion protein is contemplated. The polynucleotide encoding the CD134L moiety of the fusion protein may be human CD134L, a fragment, homologous, or orthologous protein thereof (i.e. functional equivalent). In particular, the polynucleotide encoding the CD134L moiety of the fusion protein may be any polynucleotide hybridisable under stringent conditions, preferably under highly stringent conditions, to a polynucleotide comprising the nucleotide sequence shown in SEQ ID NO: 1 or SEQ ID NOs: 22-25.

As used herein, the terms "gene" and "recombinant gene" refer to nucleic acid molecules which may be isolated from chromosomal DNA, which include an open reading frame encoding a protein, e.g. human CD134L and any homologous, orthologous, and functionally equivalent sequences thereof. A gene may include coding sequences, non-coding sequences, introns and regulatory sequences. Moreover, a gene refers to an isolated nucleic acid molecule as defined herein.

A nucleic acid molecule, such as a nucleic acid molecule having the nucleotide sequence shown in SEQ ID NO: 1, SEQ ID NOs: 22-25 or a functional equivalent thereof may be isolated using standard molecular biology techniques and the sequence information provided herein. For example, a nucleic acid sequence having the sequence shown in SEQ ID NO: 1 or SEQ ID NOs: 22-25 can be isolated using standard hybridization and cloning techniques (e.g., as described in Sambrook, J., Fritsh, E. F., and Maniatis, T. Molecular Cloning: A Laboratory Manual 2nd, ed., Cold Spring Harbor Laboratory, Cold Spring Harbor Laboratory Press, Cold Spring Harbor, N.Y., 1989).

Some of nucleotide sequences that are functionally equivalent to the nucleotide sequence of SEQ ID NO: 1 include, but are not limited, to the nucleotide sequences of SEQ ID NOs: 22-25, and homologues sequences thereof. In some embodiments, the functional equivalents of the human CD134L nucleotide sequence include different CD134L nucleotide sequences having the nucleotide sequence identity of at least 30% to the human CD134L nucleotide sequence. In some embodiments, the nucleotide sequence identity present in the functional equivalents of the human CD134L nucleotide sequence sequence is at least about 20%, 25%, 30%, 35%, 40%, 45%, 50%, 55%, 60%, 65%, 70%, 75%, 80%, 85%, 90%, 95%, 99%, and any intervening number of nucleotide sequence identity to the human CD134L nucleotide sequence.

Moreover, a nucleic acid molecule encompassing all or a portion of the nucleic acid sequence shown in SEQ ID NO: 1 or, SEQ ID NOs: 22-25 can be isolated by the polymerase chain reaction (PCR) using synthetic oligonucleotide primers designed based upon the sequence information contained in SEQ ID NO: 1 or, SEQ ID NOs: 22-25.

In another embodiment, an isolated nucleic acid molecule may comprise a nucleic acid molecule which is a complement of the nucleotide sequence shown in SEQ ID NO: 1, SEQ ID NOs: 22-25 or a functional equivalent of these nucleotide sequences. A nucleic acid molecule that is complementary to another nucleotide sequence is one that is sufficiently complementary to the other nucleotide sequence such that it can hybridize to the other nucleotide sequence thereby forming a stable duplex.

In one aspect, isolated nucleic acid molecules may be provided that encode a polypeptide as described herein or a functional equivalent thereof such as a biologically active fragment or domain, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules.

Also referred herein are isolated nucleic acids that comprise DNA or RNA sequences (polynucleotides) encoding the CD134L moiety of the fusion protein. The nucleic acids may further comprise vectors for expression of the fusion protein of the invention. It is understood by one of ordinary skill in the art that because of the degeneracy in the genetic code, substitutions in the nucleotide sequence may be made which do not result in changes in the encoded amino acid sequence. It is further understood by one of ordinary skill in the art that both complementary strands of any DNA molecule described herein are included within the scope.

As used herein, the term "vector" refers to a vehicle made of a polynucleotide or which contains a polynucleotide which can transfer a polynucleotide sequence or gene of interest to a target cell. The vector may be a "viral vector" or a "plasmid vector" or may combine both properties in one construct. Examples of a vector include vectors which are capable of self replication or capable of being incorporated into a chromosome within host cells (e.g., prokaryotic cells, yeast, animal cells, plant cells, insect cells, whole animals, and whole plants), and contain a promoter at a site suitable for transcription of a polynucleotide or gene.

As used herein, the term "expression vector" refers to a nucleic acid sequence comprising a structural gene and a promoter for regulating expression thereof, and in addition, various regulatory elements in a state that allows them to operate within host cells. The regulatory element may include, preferably, terminators, selectable markers such as drug-resistance genes (e.g., a kanamycin resistance gene, a hygromycin resistance gene, etc.), and enhancers. It is well known to those skilled in the art that the type of an organism, expression vector and the type of a regulatory element may vary depending on the host cell.

As used herein, the term "promoter" refers to a base sequence which determines the initiation site of transcription of a gene and is a DNA region which directly regulates the frequency of transcription. Transcription is started by RNA polymerase binding to a promoter. The DNA insert should be operatively linked to an appropriate promoter, such as the SV40 early and late promoters, CMV promoter (immediate-early promoter-regulatory region of human cytomegalovirus) and promoters of retroviral LTRs, such as those of the Rous sarcoma virus ("RSV"), metallothionein promoters, such as the mouse metallothionein-I promoter, to name a few. The skilled person will know other suitable promoters. Such promoters are known in the art. The expression constructs may contain sites for transcription initiation, termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

As used herein, the terms "transformation", "transduction" and "transfection" are used interchangeably unless otherwise mentioned, and refers to introduction of a nucleic acid into host cells. As a transformation method, any technique for introducing DNA into host cells can be used, including various well-known techniques, such as, for example, the electroporation method, the particle gun method (gene gun), the calcium phosphate method, and the like.

As used herein, the term "transformant" refers to the whole or a part of an organism, such as a cell, which is produced by transformation. Examples of a transformant include prokaryotic cells, such as bacteria (e.g. *Escherichia coli*), and eukaryotic cells such as yeast, animal cells, plant cells, insect cells and the like. Transformants may be referred to as transformed cells, transformed tissue, transformed hosts, or the like, depending on the subject. As used herein, all of the forms are encompassed, however, a particular form may be specified in a particular context.

Hybridisation

As used herein, the term "hybridizing" is intended to describe conditions for hybridization and washing under which nucleotide sequences at least about 20%, 25%, 30%, 35%, 40%, 45%, 50%, 55%, 60%, 65%, 70%, 75%, 80%, 85%, 90%, 95%, 96%, 97%, 98%, or 99% homologous to each other typically remain hybridized to each other.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., preferably at 60° C. and even more preferably at 65° C.

Highly stringent conditions include, for example, hybridizing at 68° C. in 5×SSC/5×Denhardt's solution/1.0% SDS and washing in 0.2×SSC/0.1% SDS at room temperature. Alternatively, washing may be performed at 42° C.

The skilled artisan will know which conditions to apply for stringent and highly stringent hybridisation conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) resides, would not be included in a polynucleotide used to specifically hybridize to a portion of a nucleic acid, since such a polynucleotide would hybridize to any nucleic acid molecule containing a poly (A) stretch or the complement thereof (e.g., practically any double-stranded cDNA clone).

Antibodies

Production of antibodies are provided, such as monoclonal or polyclonal antibodies that specifically bind to the antigenic protein moiety of the fusion protein encoded by one or more expression vectors disclosed herein.

As used herein, the term "antibody" (Ab) or "monoclonal antibody" (Mab) is meant to include intact molecules as well as antibody fragments (such as, for example, Fab and F(ab')2 fragments) which are capable of specifically binding to an antigenic protein. Fab and F(ab')2 fragments lack the Fc fragment of intact antibody, clear more rapidly from the circulation, and may have less non-specific tissue binding of an intact antibody (Wahl et al., *J. Nucl. Med.* 24:316-325 (1983)). Thus, these fragments are preferred.

The antibodies may be prepared by any of a variety of methods. For example, cells expressing a fusion protein having an antigenic protein or an antigenic fragment thereof fused C-terminally to CD134L can be administered to an animal in order to induce the production of sera containing polyclonal antibodies. In one method, the antibodies are monoclonal antibodies (or specific binding fragments thereof). Such monoclonal antibodies can be prepared using hybridoma technology (Kohler et al., *Nature* 256:495 (1975); Kohler et al., *Eur. J. Immunol.* 6:511 (1976); Hammerling et al., In: *Monoclonal Antibodies and T-Cell Hybridomas*, Elsevier, N.Y., pp. 563-681 (1981)). In general, such procedures involve immunizing an animal (preferably a mouse) with a protein or with a cell expressing a protein. The splenocytes of such mice are extracted and fused with a suitable myeloma cell line. Any suitable myeloma cell line may be employed; however, it is preferably to employ the parent myeloma cell line (SP20), available from the American Type Culture Collection, Rockville, Md. After fusion, the resulting hybridoma cells are selectively maintained in HAT medium, and then cloned by limiting dilution as described by Wands et al. (*Gastro-enterology* 80:225-232 (1981)). The hybridoma cells obtained through such a selection are then assayed to identify clones, which secrete antibodies capable of binding the respective protein antigen.

In particular, various host animals can be immunized by administering the expression vector encoding the fusion protein carrying the a polypeptide of interest. Examples of suitable host animals include rabbits, mice, guinea pigs, and rats. Such antibodies can be of any immunoglobulin class including IgG, IgM, IgE, IgA, IgD, and any subclass thereof. The hybridomas producing the mAbs can be cultivated in vitro or in vivo.

Once produced, polyclonal or monoclonal antibodies are tested for specific recognition of a protein disclosed herein or a functional equivalent thereof in an immunoassay, such as a Western blot or immunoprecipitation analysis using standard techniques, e.g., as described in Ausubel et al., supra. Antibodies that specifically bind to a protein disclosed herein or functional equivalents thereof may also be useful.

Preferably, antibodies are produced using fragments of the protein(s) disclosed herein, wherein the fragments may be likely to be antigenic, by criteria such as high frequency of charged residues. For example, such fragments may be generated by standard techniques of PCR, and then cloned into the expression vector encoding the fusion protein.

Alternatively, techniques described for the production of single chain antibodies (U.S. Pat. Nos. 4,946,778 and 4,704,692) can be adapted to produce single chain antibodies against a protein disclosed herein or functional equivalents thereof. Kits for generating and screening phage display libraries are commercially available e.g. from Pharmacia.

Polyclonal and monoclonal antibodies that specifically bind a protein or functional equivalents thereof can be used, for example, to detect expression of a gene encoding a protein according or a functional equivalent thereof. Examples of suitable assays include, without limitation, Western blotting, ELISA's, radio immune assays (RIA's), and the like.

By "specifically binds" is meant that an antibody recognizes and binds a particular antigen but does not substantially recognize and bind other unrelated molecules in a sample.

Antibodies can be purified, for example, by affinity chromatography methods in which the polypeptide antigen is immobilized on a resin.

An antibody (e.g. a monoclonal antibody) directed against a protein disclosed herein can be used to isolate the protein by standard techniques, such as affinity chromatography or immunoprecipitation. Moreover, such an antibody can be used to detect the protein (e.g., in a cellular lysate or cell supernatant) in order to evaluate the abundance and pattern of expression of the protein.

Coupling the antibody to a detectable substance can facilitate detection. Examples of detectable substances include various enzymes, prosthetic groups, fluorescent materials, luminescent materials, bioluminescent materials, and radioactive materials. Examples of suitable enzymes include horseradish peroxidase, alkaline phosphatase, [beta]-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin.

Examples 1-12: Human CD134L

Example 1

Preparation of an Expression Vector

An expression vector, referred to as "pCD1-CD134L" was constructed in order to determine if CD134L could be used as a carrier for the cell surface expression of antigens which have been bound to its carboxy terminus.

To construct this vector, pCD1 was used. pCD1 is a derivative of pEBS-PL, taught by Bontron, et al., *Mol. Cell Biol.*, 17:4249-4258 (1997), incorporated by reference, which encodes a β-lactamase gene to permit bacterial selection, and "hph76," which is a gene which provides hygromycin resistance, driven by the SV40 early promoter.

To prepare the expression vector, cDNA for human type II transmembrane protein CD134L cDNA, as taught by Miura, et al., *Mol. Cell Biol.*, 11:1313-1325 (1991), incorporated by reference in its entirety, followed by a (G$_4$S)$_3$ (SEQ ID NO: 31) coding linker, an XbaI/NotI cloning site, and a stop codon, were inserted downstream of the SR alpha promoter (Takebe, et al., *Mol. Cell Biol.*, 8:466-472 (1988)), using SalI and KpnI restriction sites.

To elaborate on this insert, it was obtained via RT-PCR, using well known methods, on mRNA that had been extracted from EBV immortalized human B lymphocytes that expressed CD134L. The oligonucleotide primers of SEQ ID NO: 3 and 4 were used in the RT-PCR in order to amplify the polynucleotide having the sequence shown in SEQ ID NO: 1 encoding human CD134L protein. SEQ ID NO: 2 shows the amino acid sequence of human CD134L.

Following this, antigenic domains from human proteins c-Myc, VGRP-1, and CD94 as well as either a portion of tick calreticulin, or a protein of Vaccinia virus were cloned into this vector, with the ORF encoding the antigen being cloned in fusion, downstream of the linker, using the XbaI and NotI restriction sites referred to, supra.

Example 2

Preparation of Nucleic Sequences Encoding the Antigenic Moiety

This example elaborates on the antigens referred to supra. Portions of 5 different antigens were cloned using PCR into the pCD1-CD134L vector. Specifically, cDNA encoding amino acids 410-419 of c-Myc; 21-93 of UGRP-1, 36-179 of CD94, 17-413 of tick calreticulin ("IRCAL"), and 48-87 of Vaccinia virus A56 were cloned into the vector described supra, using the primers of SEQ ID NOs: 5-17. These primers were designed to create XbaI and NotI restriction sites at the 5' and 3' ends, in order to clone them in frame with the (G$_4$S)$_3$ (SEQ ID NO: 31) linker.

In detail, a cDNA encoding *Ixodes ricinus* calreticulin (IRCAL) (Xu et al., *J Parasitol* 91, 1326-31 (2005)) was produced by RT-PCR reactions on mRNA purified from tick salivary glands as described elsewhere (Daix et al., *Insect Mol Biol* 16, 155-66 (2007)). RT reactions were performed on 150 ng of *I. ricinus* salivary gland mRNA using SuperScript III First-Strand Synthesis System for RT-PCR Kit (Invitrogen). The Oligo(dT)$_{20}$ provided in the kit was used for this reaction. Finally, cDNA product was amplified by PCR using the IRCALfw1 primer (SEQ ID NO: 11) and the reverse primer Oligo(dT)$_{20}$. RT-PCR products were TA-cloned into the pGEM-T easy vector (Promega) and sequenced. Next, IRCAL ORF was cloned by PCR in the pcDNA3.1(+) eucaryotic expression vector (Invitrogen) resulting in pcDNA3.1-IRCAL. The PCR reaction was performed using the forward IRCALfw2 primer (SEQ ID NO: 12) containing a 5' NheI site and nucleotides 1-17 (nucleotides 1-3 encode the initiation methionine) and the reverse IRCALrev2 primer (SEQ ID NO: 13) corresponding to the ORF 3' end (nucleotides 1221-1239), the stop codon, and a XbaI site.

The Human c-Myc epitope corresponding to AA 410-419 was created by PCR using the cMycfw and cMycrev primers (SEQ ID NO: 5 and SEQ ID NO: 6). Human Uteroglobin-related protein 1 (UGRP-1) (A21 to V93) coding sequence without signal peptide was recovered from a subcloned cDNA kindly provided by Dr A. Bernard (Unit of Industrial Toxicology and Occupational Medicine, Université Catholique de Louvain) (Niimi et al., Mol *Endocrinol*. 15, 2021-2036 (2001)). Human CD94 coding sequence corresponding to the extracellular domain (T36 to I179) of the protein was amplified by PCR using a human CD94 subclone as template (ATCC 99596). IRCAL ORF without its signal peptide was amplified by PCR using pcDNA3.1-IRCAL as template, the forward primer IRCALfw3 (SEQ ID NO: 14) containing a 5' XbaI site and nucleotides 49-57 and the reverse primer IRACLrev3 (SEQ ID NO: 15) corresponding to the 3' end of the ORF (nucleotides 1225-1239) and a 5' NotI site. The amplicon was then cloned by XbaI/NotI digestion into the pCD1-CD134L vector, resulting in pCD1-CD134L-IRCAL. A region of the A56 protein (W48 to I87) encoded by VV Lister strain was amplified by PCR using the primers shown in SEQ ID NO: 16 and SEQ ID NO: 17 and viral NA as template. The amplified region is conserved amongst various orthopoxviruses including Variola virus and is part of the extracellular domain of the protein.

Once these antigenic regions were cloned into the vector, P1.HTR cells (Van Pel, et al., *Somat. Cell Mol. Genet.*, 11:467-75 (1985)) were transfected using the calcium phosphate precipitation method described by Van Pel, et al., supra. In addition, rat myeloma cells, IR983F described by Brazin, et al., in Peeters, ed. Protides of the Biological Fluids 29$^{th}$ Colloquium (Pergamin Press, 615-618 (1982), and "Crandell Reese feline kidney," or "CRFK" cells, obtained from the ATCC or "ATCC CCC-94" were transfected via a standard electroporation protocol, i.e., 1 pulse at 40 µsec at 1000 volts.

Twenty-four hours post transfection, the cells were selected via standard limiting dilution culture, in minimal essential medium, using 500 µg/ml hygromycin β.

Example 3

Immunofluorescent Staining of Cells Transformed with the Construct

Following the cell selection described supra, hygromycin resistant cells were tested to determine if they expressed CD134L and the fused antigen on their surfaces.

Indirect immunofluorescent stainings were performed on three types of samples: cells in suspension, cell monolayers grown on glass coverslips and micro-dissected tick salivary glands. All types of samples were fixed in phosphate-buffered saline (PBS) (PBS: 3 mM KCl, 1.5 mM KH$_2$PO$_4$, 0.14 M NaCl, 6.5 mM Na$_2$HPO$_4$, pH 7.2) containing 4% (w/v) paraformaldehyde (Merck) for 15 min on ice and then 30 min at room temperature. Where indicated, after washing with PBS, the samples were permeabilized in PBS containing 0.1% (w/v) NP40 (Fluka) for 20 min at 37° C. Immunofluorescent stainings (incubation and washes) were performed in PBS containing 10% (v/v) FCS (PBSF). The samples were incubated at 37° C. for 45 min with primary antibodies. The following primary antibodies were used: a rat monoclonal antibody (Mab) raised against human CD134L (LO-CD134L, Experimental Immunology unit UCL), a mouse Mab raised against human c-Myc (9E10, Becton Dickinson), a mouse Mab raised against human UGRP-1 (MhUGRP-1, Experimental Immunology unit UCL), a mouse Mab raised against human CD94 (HP-3D9, Becton Dickinson) and sera from immunized animals (rat and mice). After three washes, samples were incubated at 37° C. for 30 min with the appropriate secondary conjugate. The following secondary conjugates were used: a FITC-conjugated mouse Mab anti-rat k light chain (MARK-1, Experimental Immunology unit UCL) and an Alexa Fluor® 488 goat anti-mouse IgG (Invitrogen). After three washes with PBSF and a final wash with PBS, samples were either mounted (cell monolayers grown on glass coverslips and micro-dissected tick salivary glands) before microscopic examination (Vanderplasschen et al., Proc Natl Acad Sci USA 95, 7544-9 (1998)) or were analysed by flow cytometry.

The results showed that the fusions to the antigenic proteins did not prevent cell surface expression of CD134L, when fused to its carboxy terminus, and that the fused antigens were also expressed on the cells surfaces (FIG. 2).

Example 4

Animal Immunisation

The data from the prior examples establish that fusion of antigens at the carboxy terminus of a type II protein such as CD134L is an efficient method to induce cell surface expression. Type II carriers, like CD134L, permit the cloning of an antigen in frame with the carboxy terminus, which avoids interference with the anchor signal at the N terminus.

These results suggested testing the potential of these fusion vectors in generating antibodies.

Female Balb-c mice (H-$2^d$), aged between 6 and 8 weeks and a three month old LOU-C rat were used for immunizations with p1.HTR and IR983F cell lines, respectively. All the animals were from specific-pathogen-free colonies bred at the Université catholique de Louvain (Brussels, Belgium) and were submitted to protocols approved by the Institutional Animal Care and Use Committee of the University (Louvain and Liege, Belgium). Balb-c mice were injected subcutaneously with $3.10^5$ P1.HTR cells stably transfected with pCD1-CD134L-IRCAL without any adjuvant. They were then boosted 2 times with $2.10^6$ cells intraperitoneously at two weeks interval. Mice were sacrified 2 weeks after the last boost. A LOU-C rat was injected intraperitoneously with $10^7$ IR983F cells stably transfected with pCD1-CD134L-A56. Cells were irradiated (5 Gy) before injection in order to avoid their invasiveness in vivo. The immunization was repeated 2 times at two weeks intervals. For the first immunization, cells were suspended in complete Freund's adjuvant. For the 2 last immunizations, cells were suspended in incomplete Freud's adjuvant. Rats were sacrificed 3 days after the last immunization. Serum was collected for serological analysis and the spleen was harvested for Mab production.

Figure 4:
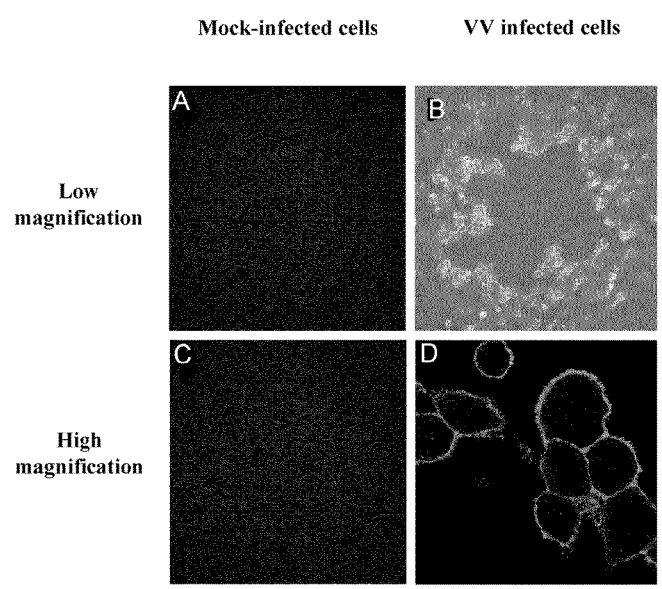
FIG. 4 shows the production of rat Mabs raised against VV A56. Rat Mab A56VV1 raised against VV A56 was one out of the 7 Mabs obtained from a single fusion after immunization with live cells expressing the antigen fused to CD134L. The reactivity of the Mab was tested by indirect immunofluorescent staining of RK13 cells mock-infected or infected cells (Lister strain of VV). The side of panels A-B and C-D corresponds to 1000 and 175 µm of the specimen, respectively.

Rat Mabs were produced as described elsewhere (Bazin, supra). Screening of hybridomas was performed in three steps. Firstly, IR983F cells stably expressing CD134L-A56 were treated for indirect immunofluorescent staining as described above using supernantant of hybridomas as primary antibodies and MARK1-FITC as secondary antibody. Positive staining was detected by flow cytometry. The flow cytometry patterns of the positives clones were similar to these depicted on FIG. 2. Secondly, to determine whether the positive clones secreted antibodies raised against the CD134L carrier or the A56 domain, IR938F cells stably expressing the CD134L (without fused antigen) were stained and analysed (selection of negative clones). Finally, anti-VV A56 hybridomas were confirmed by indirect immunofluorescent staining of RK13 cells infected with the Lister strain of VV (Vanderplasschen et al., *Proc Natl Acad Sci USA* 95, 7544-9 (1998)); mock-infected cells were used as control (FIG. 4).

The collected mice sera were analyzed for the presence of antibodies specific for the respective antigen via indirect immunofluorescence, as described supra. All of the mice that had been immunized (a total of 10), had detectable antibodies against IRCAL, at titers ranging from 1/512 to 1/4096.

The mouse sera were tested for the presence of antibodies by contact with tick salivary glands. Confocal examination showed that the antibodies recognized a protein that was expressed abundantly in the endoplasmic reticulum and secretory vesicles of the salivary glands.

Serum from the rats contained a high titer (1/8192) of anti-Vaccinia antibodies. As noted, supra, the spleen from the rat was used to produce hybridomas, and then monoclonal antibodies, in accordance with Bazin, supra, incorporated by reference. The hybridomas were screened via indirect immunofluorescence staining of RK13 cells that had been infected with the Lister strain of Vaccinia virus, in accordance with Vanderplasschen, et al., *Proc. Natl. Acad. Sci. USA*, 97:5756-61 (1998).

A single fusion produced seven mAbs which stained the Vaccinia virus plaques strongly.

Example 5

Induction of Auto-Antibodies Raised Against Self Antigens IL-22BP and IL-9

Further experiments were carried out to use the methods of the prior experiments to generate antibodies against IL-22BP, and IL-9.

Coding sequences corresponding to mature murine IL-9 and IL-22BP were amplified from their original cDNA, as described by Van Snick, et al., *J. Exp. Med.*, 169:363-368 (1989), and Weiss, et al., *Genes Immun.*, 5:330-336 (2004), incorporated by reference, via PCR, with primers designed to introduce the XbaI restriction sites. These forward primers are set forth in SEQ ID NOs: 18 and 19, while the reverse primers, which introduced a NotI restriction site and mutated the stop codon, are set forth at SEQ ID NOs: 20 and 21.

The PCR products were digested with XbaI and NotI, and then ligated into the pCD1 plasmid which already contained the other elements referred to supra. The result was a single, open reading frame, encoding a fusion protein between CD134L and IL-9 or IL-22BP.

Example 6

Immunofluorescent Staining of Cells Transformed with the Gene Encoding the Fusion Protein Comprising IL-22BP or IL-9

The resulting vectors were then transfected into P1.HTR cells, using the methods described supra. Twenty-four hours after transfection, selection of cell clones was performed by limiting dilution culture with 500 µg/ml hygromycin B. Cell clones were screened by flow cytometry with a rat monoclonal antibody specific for human CD134L (clone FCL212-1E4), followed by a fluorescein isothiocyanate (FITC)-conjugated mouse anti-rat kappa light chain antibody (clone MARK-1). Alternatively, positive clones were identified by using as primary antibody serum from mice previously immunized with human CD134L, and as secondary antibody, goat anti-mouse FITC-conjugated immunoglobulins. Fluorescence intensity was measured for cells incubated with or without the primary antibody, and cell clones exhibiting the higher fluorescence shift between these two conditions were chosen for injection to mice.

The cells were screened via flow cytometry, also as described, supra. Those cells showing the highest fluorescence shift when comparing results obtained with and without the primary antibody, were used in the following experiments.

Example 7

Animal Immunization Using Cells Transformed with the Gene Encoding the Fusion Protein Comprising IL-22BP or IL-9

Experimental animals were then injected with the cells described supra, to ascertain whether or not antibodies were generated specific to IL-22BP or IL-9.

Syngeneic DBA/2 mice received six, bi-weekly injections of increasing numbers of cells. No adjuvant was used. The first 2 injections were made to the footpads, subcutaneously, and the last four, intraperitoneally. The first injected consisted of $1\times10^5$ cells, and was followed by injections of the same number, then two injection of $1\times10^6$ cells, and then two injections of $5\times10^6$ cells. Mice were bled every two weeks in order to monitor serum antibody titers.

After the first five injections, serum samples were taken from the immunized mice, and the samples were diluted, 1/450. The samples were then incubated, with one of two cell lines (BW5147 or BW.IL-22BP). BW 5147 cells express a cell surface variant of murine IL-22BP. These cells were produced by transfecting BW5147 parent cells with an expression vector that encodes IL-22BP ORF, in fusion with the transmembrane domain of the PDGF receptor. A stably transfected clone known as BW.IL-22BP was also used. See de Mauro, et al., *FEBS Lett.*, 583:1071-1077 (2009), incorporated by reference.

The sera were incubated with the cells and antibodies were detected using a commercially available, goat anti-mouse fluorescent antibody. Anti IL-22BP antibodies could be found in the sera of the immunized mice but not in controls.

Example 8

Inhibition of IL-9 Activity In Vivo

Following the experiments described supra, additional work was carried out to determine if any of the antibodies were inhibitory of IL-22BP function. To determine this, BW.IL22-BP cells were pre-incubated with serial dilutions of the immune sera described supra, for 30 minutes, at room temperature. Then, 3.5 ng/ml of biotinylated murine IL-22 was added, and the mixture was incubated for 45 minutes, at 4° C. Cells were then washed and incubated with phycoerythrin conjugated streptavidin for 30 minutes, at 4° C. The samples were then subjected to standard, FACS analysis.

Sera from control mice did not impact the binding of IL-22, while serum from 2 of 3 mice that had been immunized did significantly antagonize the IL-22 binding, with half-maximal exhibition occurring at serum dilutions of 1/400-1/1,000.

These experiments thus establish that the immunization methodology described herein can produce inhibitory antibodies.

Example 9

Inhibitory Effect of Autoantibodies Directed to IL-9 In Vitro

Further conformance of the efficacy of the method described herein came from experiments in which IL-9 was fused to hCD134L, as described supra. Immunization was carried out as was described for IL-22BP constructs, supra, and inhibitory antibodies were detected using the TS1 bioassay described by Uyttenhove, et al., *Eur. J. Immunol.*, 36:2868-2874 (2006), incorporated by reference.

Sera from all immunized mice inhibited IL-9 induced proliferation of TS-1 cells, at dilutions up to at least 1/1350. The inhibition was shown to be specific, because IL-4 induced proliferation, was not affected at all.

Example 10

Inhibitory Effect of Autoantibodies Directed to IL-9 In Vivo

These experiments were designed to determine if antibodies produced in accordance with methods disclosed herein had inhibitory effects in vivo.

DBA/2 mice were immunized, intraperitoneally, with either contrive cells P1-HTR-CD134L, or P1-HTR-CD134L-mIL-9. The test animals received three intraperitoneal injections of IL-9 (150 ng the first two days, in succession, 30 ng the third day). The mice were bled before the first injection and then at the third day. The concentration of mast cell specific protease mMCP-1 was measured, using commercially available products. (The amount of mMCP-1 is an indicator of IL-9 activity).

The IL-9 induced a significant increase in mMCP-1 levels in control mice, and none in the mice which received the cells transfected with CD134L-mIL-9, thus confirming inhibitory efficacy in vivo.

Example 11

Histocompatibility Restriction

These experiments were designed to determine if histocompatibility antigens are a factor in the methodology discussed herein.

To test this, both syngeneic DBA/2 and allogeneic DBA/2xC57BL/6 mice were treated as described supra, and the antibodies produced were tested for inhibitory effect.

Only half of the C57/BL6 mice produced relevant antibodies, and with low titers, while high titers were found in all DBA/2 and C57BL/6F1 mice, which possess both haplotypes.

Example 12

Immunization of Subject Animal Using Electrotransfer of CD134L Fusion Constructs As a response to the MHC haplotype restriction observed, an electro transfer method was used, in order to induce expression of the fusion construct.

The plasmid pCDNA3, which is commercially available, was used. Vectors were constructed, as described supra, with the CD134L coding sequence fused to IL-22BP. The vectors were then transformed into *E. coli* in order to produce large quantities of the vectors, which were purified using standard methods.

8 weeks old naïve BALB/c mice were prepped for injection by being shaved on their thighs, the day before, and with an injection of alum adjuvant diluted 3 fold in saline buffer, which was then injected in both tibial cranial muscles (25 μl/muscle), of each mouse.

The mice then received 3 electro injections of either the hCD134L-mIL-22BP expression vector or the control, at 3 week intervals. The electro injections were in accordance with Bloquil, et al., *BMC Biotechnol.*, 6:16 (2006), and Vandermeulen, et al., *J. Control Release*, 124:81-87 (2007), incorporated by reference. In brief, 10 μg of the DNA, in 25 μl of saline buffer, was injected into both tibialis of each mouse, all of which had been anesthetized. A 6 mm spaced electrode was then used to deliver 8 electric pulses of 120V (200 V/cm, 20 ms, 2 Hz), to each leg.

Figure 5:
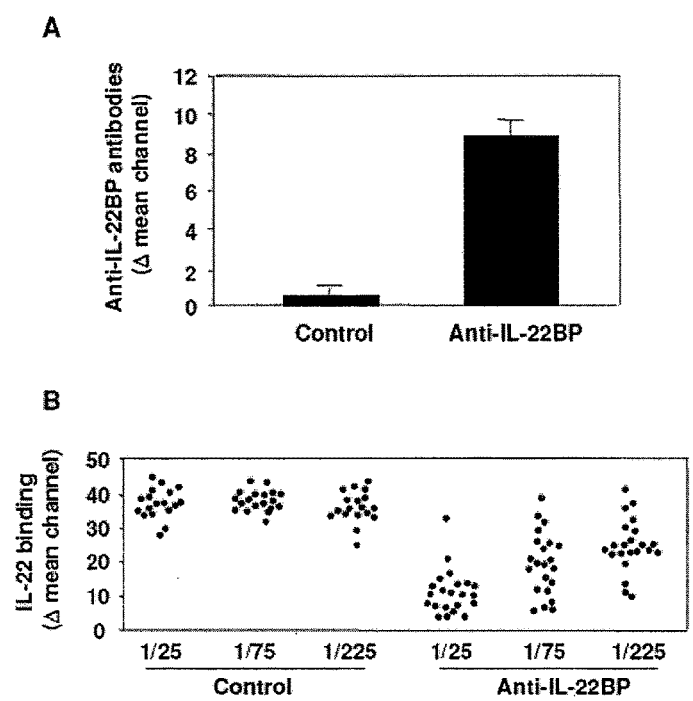
FIG. 5 shows the detection of specific and inhibitory anti-IL-22BP antibodies after DNA electrotransfer. Balb/c mice were immunized three times using electrotransfer with either pCDNA3 (coding for a hCD134L-mIL-22BP fusion protein) or a control vector. Panel A summarizes the results of the analysis of specific antibodies using the flow cytometry assay. Results are presented as mean of delta mean channels for each group (N=18 for control mice, 22 for anti-IL-22BP mice) at a 1/450 dilution. Panel B: the same serum samples were assessed for inhibiting the binding of biotinylated IL-22 on BW.IL22BP cells. IL-22 binding to membrane IL-22BP was determined using the delta mean channel between biotinylated-IL-22 labeled cells preincubated or not with serum dilutions.

Fourteen days after the last injection, animals were bled to analyze the auto antibodies produced. Most of the mice produced anti IL-22BP auto antibodies that were detectable at a dilution of 1/450, while inhibiting binding of IL-22 to IL-22BP at higher concentrations. As shown in FIG. 5, most of these mice produced anti-IL-22BP autoantibodies that could be detected at a dilution of 1/450 of the serum (FIG. 5A) and inhibited the binding of IL-22 to IL-22BP at higher concentrations (FIG. 5B). This electrotransfer procedure thereby provides an alternative to whole cell immunization for rasing relevant antibodies.

Example 13

Immune Response Against Antigens Having a Wide Range of Sizes

When peptides or antigens are not sufficiently large or complex on their own to induce an immune response and produce antibodies, it may be useful to use a carrier protein. The carrier protein, because it is often large and complex, may confer immunogenicity to the conjugated peptide/antigen, resulting in antibodies being produced against epitopes on the peptide/antigen and carrier. Many proteins can be used as carriers and chosen based on immunogenicity, solubility, and availability of useful functional groups through which conjugation with the peptide can be achieved in vitro. The two most commonly used carriers may include, but not limited to, keyhole limpet hemocyanin (KLH) and bovine serum albumin (BSA). The parameters used to choose the carrier may include the size of the carrier (large), the origin of the carrier (use of a "foreign" protein to maximize immunogenicity) and the ability to fuse several peptides to the carrier. KLH is a molecule composed of 350 kDa and 390 kDa subunits that associate to form aggregates ranging from 0.5 to 8 million daltons (i.e. very large). An alternative carrier is bovine serum albumin (BSA) because it is highly immunogenic and less large (67 kDa monomers which form dimers having a total size of 134 kDa) and has several sites to which peptides can be crosslinked (30 to 35 lysine residues of the carrier have primary amines that are capable of reacting with a conjugation reagent). Thus, after conjugation, the BSA molecule can contain several peptides. Another popular carrier is ovalbumin (45 kDa monomers which form dimers having a total size of 90 kDa) and which provides several sites to which peptides can be crosslinked (ovalbumin contains 20 lysine groups usable for crosslinking and 14 aspartic acid and 33 glutamic acid residues that afford carboxyl groups also usable as targets for conjugation).

The experiments below were conducted with fusion proteins comprising the full length human CD134L protein and $G_4S$ (SEQ ID NO: 30) linker fused to antigens. The CD134L polypeptide is only 24 kDa and has only one single peptide/antigen fused to it by genetic engineering. CD134L forms a trimer in the membrane. One can thus say that the final size of the CD134L is 72 kDa and that there are three peptides/antigens present in the trimer.

Surprisingly, despite the small size of the CD134L trimer and the limited number of antigens attached thereto, the fusion proteins comprising the full length human CD134L protein and $G_4S$ (SEQ ID NO: 30) linker fused to antigens having a size between 25 amino acids and 505 amino acids were able to generate a strong immune response against the antigens. Briefly, plasmid DNA encoding the CD134L+G4S (SEQ ID NO: 30) linker+ antigen sequence was amplified and purified from E. coli. The antigens were from different origins: the minimal size was 25 amino acids of a human protein and the biggest one was 505 amino acids from bacterial origin. Between these two sizes, several antigens were tested as described in the following table:

| Antigen size fused to the CD134L carrier | Origin | Immunization method |
| --- | --- | --- |
| 25 amino acid | Human | DNA + electroporation or transfected cells |
| 46 aa | Hydra | DNA + electroporation |
| 120 aa | Bacteria | DNA + electroporation |
| 244 aa | Bacteria | DNA + electroporation |
| 257 aa | Bacteria | DNA + electroporation |
| 306 aa | Fish | DNA + electroporation |
| 505 aa | Bacteria, pathogen | DNA + electroporation or transfected cells |

After purification, plasmid DNA was either used naked for electroporation (see below) or transiently transfected into cells and these cells were injected (intraperitoneal injection) into the subject animal to immunize it. For electroporation, 20 μg of plasmid DNA encoding each antigen was injected intramuscularly and electric pulses were applied to the subject animal as close as possible to the injection site. The injection/electroporation of naked DNA was performed in each leg of the animal.

For each antigen, 5 mice were used. One immunization and two boosts were performed for each animal. Two weeks after each injection/electroporation, serum was sampled and analyzed by FACS using transfected cells producing the corresponding antigen or by Elisa tests based on purified recombinant antigen. For all described antigens, polyclonal sera showed positive results. For several antigens, monoclonal antibodies were developed using standard methods as described in the patent application. Cells from spleen and lymph nodes were recovered, immortalized by generation of hybridoma with sp2 cells. These hybridoma were cultivated to accumulate antibodies in the medium and samples were tested by FACS or Elisa. Several hybridomas were positive for each antigen (at least 10 and up to 40 different hybridomas were producing antibodies able to bind specifically each antigen).

The efficiency of the CD134L fusion proteins demonstrated by the experiments described above is surprising first with respect to the size of the fusion proteins (smaller than the conventional carriers discussed above). Secondly, the above results are surprising because good results are obtained even when the CD134L sequence is from the same species as the species in which the antibodies are being generated.

It is also surprising that the ability of the CD134L fusion proteins to generate a good immune response is retained since it is expected that CD134L must form trimers in the membrane to keep its biological activity. Fusion of an additional sequence to the CD134L sequence could reduce the efficiency of forming a trimer by changing the conformation of the complete protein. However, the fusion protein promotes good immune response with antigens spanning a range of sizes between 25 and 505 amino acids. It is expected that larger antigens, such as antigens of 505 amino acids, would have a greater potential to disrupt the conformation of the protein than smaller antigens.

Finally, the efficiency of fusion proteins comprising the full length sequence of CD134L is surprising since the C-terminal end of the protein is located very close to the cell membrane. This end of the protein is used to fuse the antigen. Consequently, the antigen is located very close to the membrane and not directly presented to the immune system. Thus, one skilled in the art would expect that using a short peptide as antigen, the method will not work because the antigen would be positioned close to the cell membrane and would be covered by the CD134L protein itself. In addition, one skilled in the art would also expect that the method would not work using large antigens since the size of the antigen would impact the ability of the protein to form a trimer and to stimulate the immune system.

Contrast to the foregoing, however, as demonstrated in the experiments presented in this example, fusion proteins comprising a polypeptide comprising the membrane anchoring domain of CD134L joined to an antigen were able to efficiently generate an immune response against antigens having a wide range of sizes.

Examples 14-17: Orthologues of Human CD134L

Example 14

Identification of CD134L Sequences from Different Species, Cloning and Immunization.

Based on the human CD134L sequence, a database search using Blast (Basic Local Alignment searching Tool) was conducted to identify CD134L sequences from different species from human, i.e. orthologous to the human CD134L seuqence. Interestingly, the corresponding sequence of *Oryctolagus cuniculus* (rabbit) was identified with 64% identity. Additional research was performed and the corresponding sequences of other species were selected as the sequence from *Mus musculus* (mouse) and *Vicugna pacos* (alpaca). The sequence from *Ornithorhynchus anatinus* (platypus) appears very different from the other sequences with only 35% of match with the human CD134L sequence. FIG. 6 shows the alignment of the CD134L sequences that are orthologous to the human CD134L sequence.

As shown by this figure, the sequences from *Ornithorhynchus anatinus* and *Mus musculus* are the less conserved sequences as compared to the sequences from *Oryctolagus cuniculus* and *Vicugna pacos* with respect to the human CD134L sequence.

Next, the DNA sequences encoding each of the orthologous sequences of CD134L protein were synthesized and cloned into an expression vector under the control of the CMV promoter as described in Example 1 (supra.). Cloning the nucleotide sequences encoding the individual orthologue CD134L sequences and preparation of the expression vectors with each of the cloned CD134L encoding sequences were done with the methodology employed in the previous Example and/or the techniques available in the art.

Figure 8:
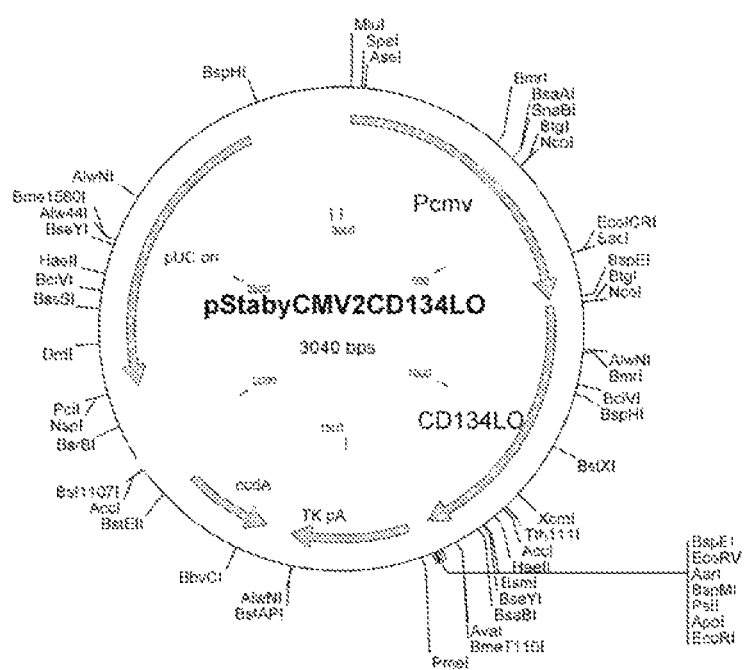
FIG. 8 shows a map of the expression vector, pStabyCMV2CD134LO that encodes a nucleic acid sequence encoding the *Oryctolagus cuniculus* CD134L polypeptide.

FIG. 8 describes one of the generated expression vectors. In particular the figure shows the map of the vector generated with the *Oryctolagus cuniculus* CD134L sequence.

The expression vectors, each of which was generated with the orthologues CD134L sequences obtained from different species (e.g. *Oryctolagus cuniculus, Oryctolagus cuniculus*, and *Vicugna pacos*, except the mouse version) were used to immunize mice by DNA electroporation as described previously in Reschner et al. (Human Vaccines & Immunotherapeutics 9:10, 1-8; October 2013). Sera of the immunized mice were collected after three injections of individual vectors and tested by flow cytometry using CHO cells transfected by the same vector. For the mouse CD134L, a commercial antibody was available and was used in the same conditions. As a negative control, an unspecific sera from mice was used.

FIGS. 9B, 9D, 9F, 9H, and 9J show examples of the results obtained with various CD134L sequences in which each of the expressed CD134L protein was found to be located in the cell membrane. As a negative control, unspecific sera was used (FIGS. 9A, 9C, 9E, 9G, and 9I). The results were also clearly positive for all CD134L sequences showing that (i) the orthologous CD134L sequences electroporated in mice were immunogenic and (ii) all orthologous CD134L proteins were expressed in CHO cells and positioned in the cell membrane.

Therefore, it is concluded that these different CD134L sequences having amino acid sequence identity of about 35% to 66% to the human CD134L sequence can have significant or substantial activity regarding their presence in/on the membrane.

Example 15

Construction of an Expression Vector Expressing a Fusion Protein of an Orthologous CD134L Protein and an Antigenic Moiety In order to test the efficiency of the different CD134L sequences regarding the presentation of an antigen, various antigen sequences were cloned in the expression vectors expressing different CD134L sequences. In some examples, the antigen sequences were inserted in the EcoRV restriction site at the end of the CD134L sequence that is commonly present in the expression vectors, expressing different orthologous CD134L sequences, creating a fusion protein composed of the corresponding CD134L, a linker having three copies of GGGGS (SEQ ID NO: 30), i.e. (GGGGS)$_3$ (SEQ ID NO: 31) amino acids, and the antigen sequence.

The construction of the different vectors was confirmed by DNA sequencing and next, the plasmid DNA of each construct was amplified in *E. coli* and transfected in NIH3T3 or CHO cells. The presentation of the antigen was analyzed by flow cytometry using antibodies specific for each antigen.

Figure 10:
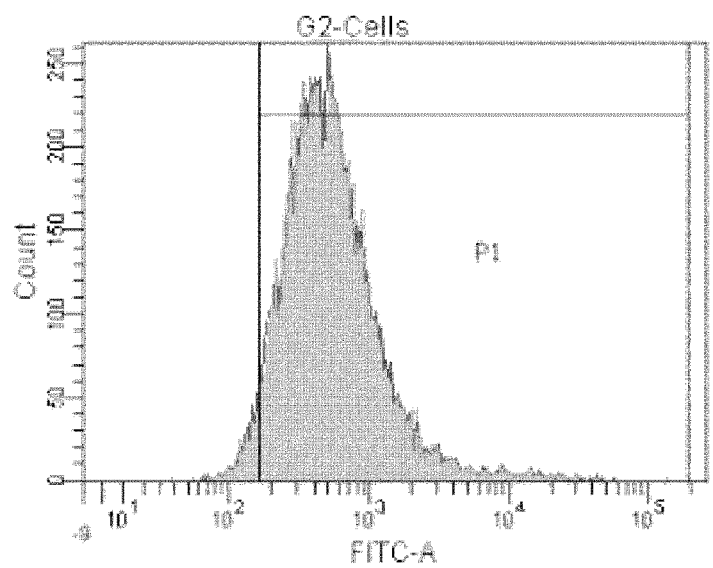
FIGS. 10A, 10B, and 10C show FACS analysis results showing the efficacy of different CD134L sequences in presenting an antigen.

FIG. 10 presents the results obtained with one antigen of 25 amino acids from a nuclear human protein that was fused with one of two different CD134L sequences (from *Mus musculus* and *Oryctolagus cuniculus*). As a negative control, untransfected NIH3T3 cells were used (FIG. 10A). As shown in this figure, the results were very close for both CD134L sequences fused to the same antigen (FIGS. 10B and 10C) despite the fact that these two CD134L sequences (from *Mus musculus* and *Oryctolagus cuniculus*) share only 41% of identity in their amino acid sequences.

Figure 11:
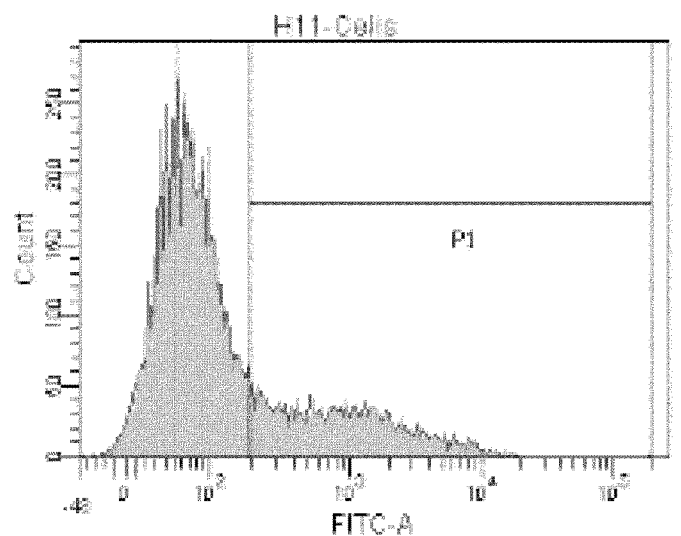
FIGS. 11A, 11B, and 11C show additional FACS analysis results showing the efficacy of different CD134L sequences in presenting an antigen fused thereto.

FIG. 11 presents the results obtained with another antigen of 244 amino acids from an antibiotic-resistance protein isolated from Enterobacteriaceae. The results are compared between two different CD134L sequences (from *Mus musculus* and *Ornithorhynchus anatinus*). As a negative control, untransfected NIH3T3 cells were used (FIG. 11A). As shown in this figure, the results were very close for both CD134L sequences fused to the same antigen (FIGS. 11B and 11C) despite the fact that they share only 29% of identity in their amino acid sequences.

Figure 12:
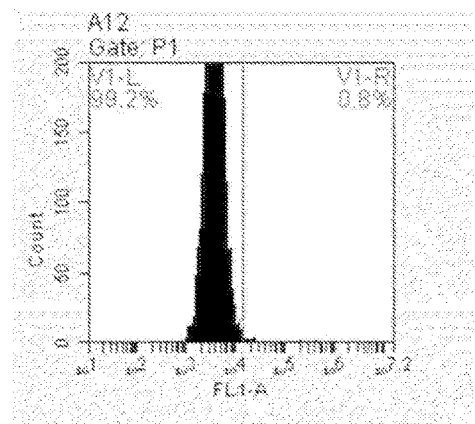
FIGS. 12A, 12B, and 12C show still additional FACS analysis results showing the efficacy of different CD134L sequences in presenting an antigen fused thereto.
Figure 12:
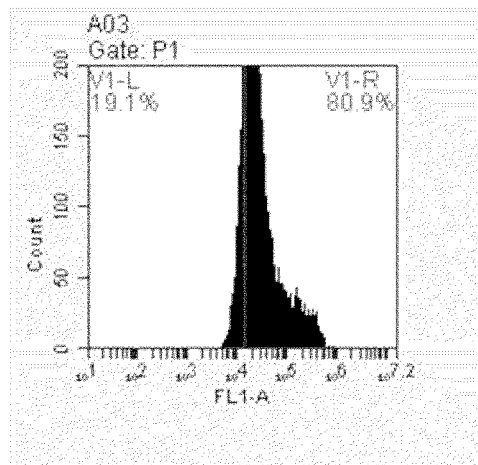
Figure 12:
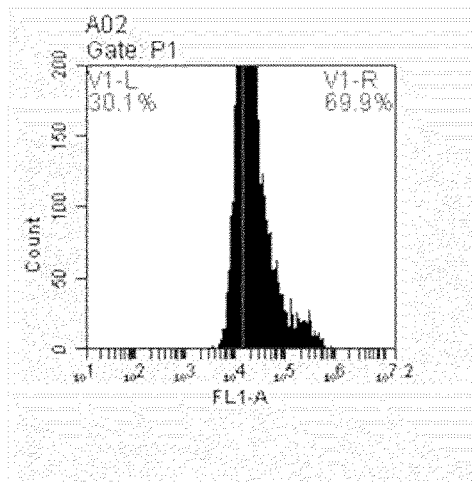

FIG. 12 presents the results obtained with another different antigen of 307 amino acids of a human receptor protein using two different CD134L sequences (from *Ornithorhynchus anatinus* and *Vicugna pacos*). As a negative control, CHO cells transfected by the *Ornithorhynchus anatinus* CD134L expression vector without the antigen were used (FIG. 12A). As shown in FIGS. 11B and 11C, surprisingly both CD134L sequences were clearly able to present the antigen sequence with a comparable efficiency even if they share only 38% of identity in their amino acid sequence.

FIG. 13 presents the sequence alignment between these two CD134L sequences from *Ornithorhynchus anatinus* and *Vicugna pacos*.

FIG. 14 presents the sequence alignment with the CD134L from *Ornithorhynchus anatinus* as a reference and shows that the least identical sequence is the *Mus musculus* sequence having only 29% amino acid identity.

The antigen presentation ability of *Ornithorhynchus anatinus* CD134L is not specific to one antigen. Indeed, as shown in FIG. 15B, the *Ornithorhynchus anatinus* CD134L was fused to another antigen and after DNA sequencing and purification, the vector was transfected in CHO cells and the presence of the antigen outside of the cell was analyzed by flow cytometry using specific polyclonal antibodies directed against the antigen. In this experiment, CHO cells were transfected with the *Ornithorhynchus anatinus* CD134L expression vector encoding the antigen that is 231 amino acids of a human proteoglycan. As a negative control, CHO cells transfected with the vector encoding only the CD134L sequence from *Ornithorhynchus anatinus* (without the antigen) were used (FIG. 15A).

Example 16

Construction of a Series of Expression Vectors Expressing a Fusion Protein of the *Mus musculus* CD134L Sequence and Different Antigenic Moieties Additionally, FIG. 16 presents the results using different antigens presented by the same CD134L, which is the *Mus musculus* CD134L sequence. In all the tested vectors, the *Mus musculus* CD134L sequence was able to present the different antigens efficiently (FIGS. 16B-16D). The different vectors encoding different antigens were used to transfect NIH3T3 cells and the antigen presentation was tested using specific polyclonal antibodies directed against the antigen. As a negative control, the expression vector expressing no antigen was used (FIG. 16A). In contrast, FIGS. 16B, 16C, and 16D show the results from staining on NIH3T3cells cells transfected with the expression vectors expressing the *Mus musculus* CD134L sequence, the linker sequence of GGGGS (SEQ ID NO: 30), and either one of the following antigens: (1) an antigen 1 that is 66 amino acids from a human transmembrane protein (FIG. 16B); (2) an antigen 2 that is 174 amino acids from a human muscarinic receptor (FIG. 16C); and (3) an antigen 3 that is 135 amino acids of a human protein expressed by neuronal precursor cells (FIG. 16D).

These results show that the same CD134L is able to present different antigens. The difference in the efficiency could be due to multiple parameters including polyclonal antibody specificity. Consequently, it may not be reasonable to merely conclude from these results that some antigens are better presented than others. However, what can be learned from these results is that these different antigens are correctly and efficiently presented by the CD134L sequence since they are recognized by specific antibodies directed against the antigens.

The experimental results provided in Examples 14 to 16 show that the different CD134L sequences from *Homo sapiens*, *Oryctolagus cuniculus*, *Mus musculus*, *Ornithorhynchus anatinus* and *Vicugna pacos* have the activity to present an antigen outside of the cell with high efficiency even if their amino acid sequences (and a fortiori, their DNA sequences) are different with a minimum of 29% of identity between two different amino acid sequences (e.g. CD134L sequences from *Ornithorhynchus anatinus* and *Mus musculus*). Moreover, a same CD134L sequence is able to present different antigens outside of the cell.

Therefore, it is concluded that different CD134L sequences having amino acid sequence identity of at least 29% to any functional CD134L sequence can have significant or substantial activity regarding their presence and the presentation of fused antigens in/on the membrane.

Example 17

Animal Immunization and Assays for Immunological Response

In order to show that the functional equivalents of CD134L, e.g. the CD134L sequences orthologous to the human CD13L sequence, are efficient to get immunological response in vivo, the experiments were conducted with two different vectors each of which encoded one of two different CD134L sequences sharing low sequence identity and fused to a same antigen.

The first vector encodes the CD134L sequence from *Homo sapiens* followed by the linker (GGGGS)$_3$ (SEQ ID NO: 31) and next the antigen sequence (244 amino acids from an antibiotic-resistance protein isolated from bacteria (Enterobacteriaceae)). The second vector is the same but the *Homo sapiens* CD134L sequence was replaced by the corresponding *Ornithorhynchus anatinus* version.

After DNA sequencing and production in *E. coli*, these two vectors were electroporated, respectively in mice as described previously in Reschner et al. (Human Vaccines & Immunotherapeutics 9:10, 1-8; October 2013) and in the previous Example 12.

In short, 8 weeks old naïve BALB/c mice were prepared for injection by being shaved on their thighs, the day before, and with an injection of alum adjuvant diluted 3 fold in saline buffer, which was then injected in both tibial cranial muscles (25 µl/muscle), of each mouse.

The mice then received 3 electro injections of the expression vector expressing either human CD134L sequence or platypus CD134L sequence at 3 week intervals. The electro injections were in accordance with Bloquil, et al., *BMC Biotechnol.*, 6:16 (2006), and Vandermeulen, et al., *J. Control Release*, 124:81-87 (2007), incorporated by reference. In brief, 10 µg of the DNA, in 25 µl of saline buffer, was injected into both tibialis of each mouse, all of which had been anesthetized. A 6 mm spaced electrode was then used to deliver 8 electric pulses of 120V (200 V/cm, 20 ms, 2 Hz), to each leg.

Fourteen days after the last injection, animals were bled to analyze the antibodies produced using ELISA assays. Most of the mice (3 out of 5 mice for *Homo sapiens* CD134L sequence and 4 out of 5 mice for *Ornithorhynchus anatinus* CD134L sequence), which were immunized with one of the two expression vectors expressing different orthologous CD134L sequences, produced the antibodies against the antigen. This proves that CD134L sequences from different origins are efficient to induce in vivo immunological response. Also, this electrotransfer procedure thereby provides an effective way to whole cell immunization for raising relevant antibodies.

As illustrated in FIG. 6, the amino acid identity of the *Ornithorhynchus anatinus* CD134L sequence to the human CD134L sequence is about 35%, yet both of these two proteins were successfully able to induce immunological response in vivo. Therefore, it can be concluded that different CD134L sequences or functional equivalents thereof having the amino acid sequence identity of at least 35% to the human CD134L sequence can have the significant or substantial activity regarding antibody production and induction of immunological response in vivo.

Example 18: Linker

Example 18

Presence or Absence of a Linker Sequence

In order to test the effect of a linker sequence, two different vectors were constructed: the first vector encoded the CD134L sequence from *Ornithorhynchus anatinus*, the (GGGGS)$_3$ (SEQ ID NO: 31) linker and the antigen sequence (244 amino acids from an antibiotic-resistance protein isolated from bacteria (Enterobacteriaceae). The second vector is the same but without the (GGGGS)$_3$ (SEQ ID NO: 31) linker (the antigen is directly fused to the end of the same CD134L sequence).

Both vectors were sequenced and amplified in *E. coli* before transfection in CHO cells. The transfected CHO cells were next analyzed by flow cytometry using specific polyclonal antibodies against the antigen.

Figure 17:
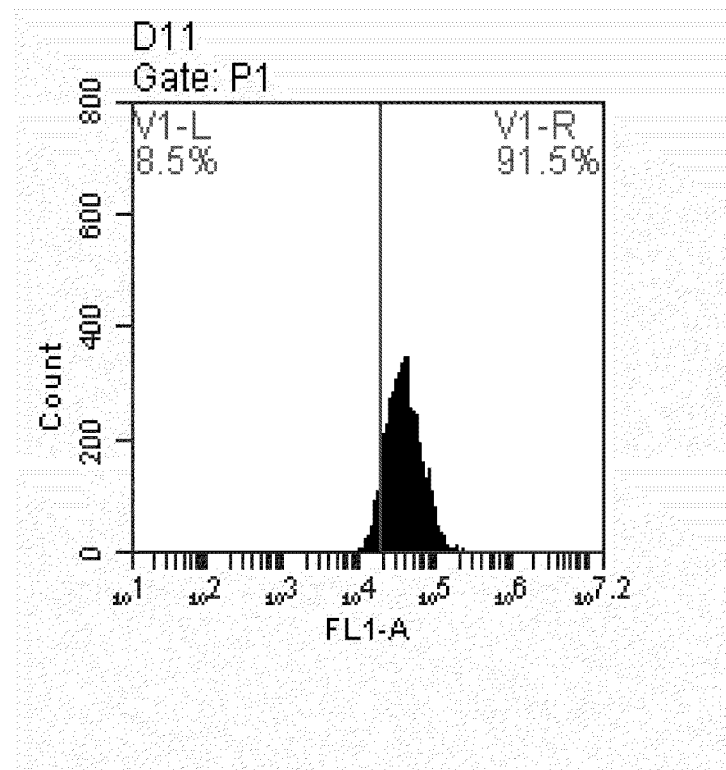
FIGS. 17A, 17B, and 17C show FACS analysis results obtained from an experiment testing the effect of a linker.

FIG. 17 presents the results for both constructs. As a negative control, untransfected CHO cells were used (FIG. 16A). The results show that the presence of the linker (GGGGS)$_3$ (SEQ ID NO: 31) is not necessary to present the antigen. The efficiency was relatively similar with and without the linker (FIGS. 17B and 17C).

The same vectors were then used to immunize mice as described above using DNA and electroporation. Next, the serum was tested by ELISA using the recombinant antigen. Most of the mice (4 out of 5 mice), which were immunized with one of the two expression vectors expressing the CD134L sequences with and without the linker (GGGGS)$_3$ (SEQ ID NO: 31), produced the antibodies against the antigen. There were no notable differences between the antigen reactivity measured in the ELISA assays between the sera obtained from the animals tested with or without linker. Therefore, these results also show that the presence of the linker (GGGGS)$_3$ (SEQ ID NO: 31) in the expression vector is not necessary to the in vivo production of antibodies against an antigen fused with a CD134L sequence.

The foregoing describes various features, which include a method for generating antibodies via the use of an expression vector which comprises a nucleic acid molecule which encodes a cell surface type II transmembrane protein, concatenated to a nucleic acid molecule which encodes an antigen of interest, such that a fusion protein is expressed, wherein the construct is in operable linkage with a promoter.

The expression vector may be administered "as is" to a subject animal, or after transformation or transfection into a cell capable of a expressing the fusion protein on its surface.

Exemplary of the cell surface type II membrane proteins disclosed herein is CD134L; however, additional proteins such as, but not being limited to CD10, CD27, CD72, CD153, CD154, and TRAIL may be employed, as well as others that are known to the skilled artisan.

The antigenic coding sequence may be all, or a part of a protein of interest, and may be foreign, or autologous, to the subject animal.

When the expression vector is transformed or transfected into a recipient cell, that cell is preferably treated so as not to be capable of proliferation within the subject.

Other aspects will be clear to the skilled artisan, and need not be reiterated here.

The terms and expression which have been employed are used as terms of description and not of limitation, and there is no intention in the use of such terms and expression of excluding any equivalents of the features shown and described or portions thereof, it being recognized that various modifications are possible within the scope of the invention.

---

What is claimed is:

1. An expression vector for generating an antibody directed to an antigen in a subject animal, the expression vector comprising a polynucleotide in operable linkage with a promoter, wherein the polynucleotide encodes a fusion protein comprising:
   (i) a CD134L polypeptide that is orthologous to human CD134L or a polypeptide having at least 95% amino acid identity to a CD134L polypeptide that is orthologous to human CD134L which anchors in a cell membrane as the N-terminal moiety of the fusion protein; and
   (ii) an antigenic protein or an antigenic fragment thereof as the C-terminal moiety of the fusion protein,
   wherein the fusion protein further comprises a linker peptide interposed between (i) and (ii).

2. The expression vector of claim 1, wherein said polypeptide of CD134L that is orthologous to human CD134L or said polypeptide having at least 95% amino acid identity to a CD134L polypeptide that is orthologous to human CD134L which anchors in a cell membrane is from a species different from the species of the subject animal.

3. The expression vector of claim 1, wherein said N-terminal moiety of the fusion protein comprises the polypeptide of SEQ ID NO: 26 or a polypeptide having at least 95% amino acid sequence identity to the polypeptide of SEQ ID NO. 26 which anchors in a cell membrane.

4. The expression vector of claim 1, wherein said N-terminal moiety of the fusion protein comprises the polypeptide of SEQ ID NO: 27 or a polypeptide having at least 95% amino acid sequence identity to the polypeptide of SEQ ID NO. 27 which anchors in a cell membrane.

5. The expression vector of claim 1, wherein said N-terminal moiety of the fusion protein comprises the polypeptide of SEQ ID NO: 28 or a polypeptide having at least 95% amino acid sequence identity to the polypeptide of SEQ ID NO. 28 which anchors in a cell membrane.

6. The expression vector of claim 1, wherein said N-terminal moiety of the fusion protein comprises the polypeptide of SEQ ID NO: 29 or a polypeptide having at least 95% amino acid sequence identity to the polypeptide of SEQ ID NO. 29 which anchors in a cell membrane.

7. The expression vector of claim 1, wherein the linker peptide is $(G_4S)_3$ (SEQ ID NO: 31).

8. The expression vector of claim 1, wherein the subject animal is a human.

* * * * *

SEQUENCE LISTING

<160> NUMBER OF SEQ ID NOS: 31

<210> SEQ ID NO 1
<211> LENGTH: 549
<212> TYPE: DNA
<213> ORGANISM: Homo sapiens

<400> SEQUENCE: 1

```
atggaaaggg tccaacccct ggaagagaat gtgggaaatg cagccaggcc aagattcgag      60
aggaacaagc tattgctggt ggcctctgta attcagggac tggggctgct cctgtgcttc     120
acctacatct gcctgcactt ctctgctctt caggtatcac atcggtatcc tcgaattcaa     180
agtatcaaag tacaatttac cgaatataag aaggagaaag gtttcatcct cacttcccaa     240
aaggaggatg aaatcatgaa ggtgcagaac aactcagtca tcatcaactg tgatgggttt     300
tatctcatct ccctgaaggg ctacttctcc caggaagtca acattagcct tcattaccag     360
aaggatgagg agcccctctt ccaactgaag aaggtcaggt ctgtcaactc cttgatggtg     420
gcctctctga cttacaaaga caaagtctac ttgaatgtga ccactgacaa tacctccctg     480
gatgacttcc atgtgaatgg cggagaactg attcttatcc atcaaaatcc tggtgaattc     540
tgtgtcctt                                                             549
```

<210> SEQ ID NO 2
<211> LENGTH: 183
<212> TYPE: PRT
<213> ORGANISM: Homo sapiens

<400> SEQUENCE: 2

```
Met Glu Arg Val Gln Pro Leu Glu Glu Asn Val Gly Asn Ala Ala Arg
 1               5                  10                  15
Pro Arg Phe Glu Arg Asn Lys Leu Leu Leu Val Ala Ser Val Ile Gln
             20                  25                  30
Gly Leu Gly Leu Leu Leu Cys Phe Thr Tyr Ile Cys Leu His Phe Ser
         35                  40                  45
Ala Leu Gln Val Ser His Arg Tyr Pro Arg Ile Gln Ser Ile Lys Val
     50                  55                  60
Gln Phe Thr Glu Tyr Lys Lys Glu Lys Gly Phe Ile Leu Thr Ser Gln
 65                  70                  75                  80
Lys Glu Asp Glu Ile Met Lys Val Gln Asn Asn Ser Val Ile Ile Asn
                 85                  90                  95
Cys Asp Gly Phe Tyr Leu Ile Ser Leu Lys Gly Tyr Phe Ser Gln Glu
            100                 105                 110
Val Asn Ile Ser Leu His Tyr Gln Lys Asp Glu Glu Pro Leu Phe Gln
        115                 120                 125
Leu Lys Lys Val Arg Ser Val Asn Ser Leu Met Val Ala Ser Leu Thr
    130                 135                 140
Tyr Lys Asp Lys Val Tyr Leu Asn Val Thr Thr Asp Asn Thr Ser Leu
145                 150                 155                 160
Asp Asp Phe His Val Asn Gly Gly Glu Leu Ile Leu Ile His Gln Asn
                165                 170                 175
Pro Gly Glu Phe Cys Val Leu
            180
```

<210> SEQ ID NO 3
<211> LENGTH: 51
<212> TYPE: DNA
<213> ORGANISM: Artificial Sequence
<220> FEATURE:
<223> OTHER INFORMATION: synthetic DNA

<400> SEQUENCE: 3

```
taacattcgt cgacatttgc taactcgaga ccatggaaag ggtccaaccc c         51
```

<210> SEQ ID NO 4
<211> LENGTH: 101
<212> TYPE: DNA
<213> ORGANISM: Artificial Sequence
<220> FEATURE:
<223> OTHER INFORMATION: synthetic DNA

<400> SEQUENCE: 4

```
tattaccatg gtcatgcggc cgctaggatg tatctagaag atccgccgcc acccgaccca    60
ccaccgcccg agccaccacc accaaggaca cagaattcac c                      101
```

<210> SEQ ID NO 5
<211> LENGTH: 45
<212> TYPE: DNA
<213> ORGANISM: Artificial Sequence
<220> FEATURE:
<223> OTHER INFORMATION: synthetic DNA

<400> SEQUENCE: 5

```
atttgctaat ctagagaaca aaaattaatt tctgaagaag attta               45
```

<210> SEQ ID NO 6
<211> LENGTH: 45

```
<212> TYPE: DNA
<213> ORGANISM: Artificial Sequence
<220> FEATURE:
<223> OTHER INFORMATION: synthetic DNA

<400> SEQUENCE: 6
atactaaatt gcggccgcta aatcttcttc agaaattaat ttttg            45

<210> SEQ ID NO 7
<211> LENGTH: 39
<212> TYPE: DNA
<213> ORGANISM: Artificial Sequence
<220> FEATURE:
<223> OTHER INFORMATION: synthetic DNA

<400> SEQUENCE: 7
atttgctaat ctagagcctt cctcatcaac aaagtgccc                   39

<210> SEQ ID NO 8
<211> LENGTH: 41
<212> TYPE: DNA
<213> ORGANISM: Artificial Sequence
<220> FEATURE:
<223> OTHER INFORMATION: synthetic DNA

<400> SEQUENCE: 8
gttaaagatg cggccgccac caagtgtgat agcgcctcca g                41

<210> SEQ ID NO 9
<211> LENGTH: 33
<212> TYPE: DNA
<213> ORGANISM: Artificial Sequence
<220> FEATURE:
<223> OTHER INFORMATION: synthetic DNA

<400> SEQUENCE: 9
atactaaatt ctagaactaa actgagtatt gag                         33

<210> SEQ ID NO 10
<211> LENGTH: 36
<212> TYPE: DNA
<213> ORGANISM: Artificial Sequence
<220> FEATURE:
<223> OTHER INFORMATION: synthetic DNA

<400> SEQUENCE: 10
atactaaatt gcggccgcaa tgagctgttg cttaca                      36

<210> SEQ ID NO 11
<211> LENGTH: 20
<212> TYPE: DNA
<213> ORGANISM: Artificial Sequence
<220> FEATURE:
<223> OTHER INFORMATION: synthetic DNA

<400> SEQUENCE: 11
cgctggccct aggtcctcat                                        20

<210> SEQ ID NO 12
<211> LENGTH: 28
<212> TYPE: DNA
<213> ORGANISM: Artificial Sequence
<220> FEATURE:
<223> OTHER INFORMATION: synthetic DNA

<400> SEQUENCE: 12
```
ccgctagcat catgcggatc gtgtgcct                                          28

<210> SEQ ID NO 13
<211> LENGTH: 30
<212> TYPE: DNA
<213> ORGANISM: Artificial Sequence
<220> FEATURE:
<223> OTHER INFORMATION: synthetic DNA

<400> SEQUENCE: 13
ggtctagatc aaagttcctc gtggtcgtgc                                        30

<210> SEQ ID NO 14
<211> LENGTH: 22
<212> TYPE: DNA
<213> ORGANISM: Artificial Sequence
<220> FEATURE:
<223> OTHER INFORMATION: synthetic DNA

<400> SEQUENCE: 14
ggcacagtct agagacccca ag                                                22

<210> SEQ ID NO 15
<211> LENGTH: 30
<212> TYPE: DNA
<213> ORGANISM: Artificial Sequence
<220> FEATURE:
<223> OTHER INFORMATION: synthetic DNA

<400> SEQUENCE: 15
gggccctgcg gccgcaagtt cctcgtggtc                                        30

<210> SEQ ID NO 16
<211> LENGTH: 33
<212> TYPE: DNA
<213> ORGANISM: Artificial Sequence
<220> FEATURE:
<223> OTHER INFORMATION: synthetic DNA

<400> SEQUENCE: 16
atactaaatt ctagatggta taaggagccc aat                                    33

<210> SEQ ID NO 17
<211> LENGTH: 36
<212> TYPE: DNA
<213> ORGANISM: Artificial Sequence
<220> FEATURE:
<223> OTHER INFORMATION: synthetic DNA

<400> SEQUENCE: 17
atactaaatt gcggccgcag ttgtaactag atcatc                                 36

<210> SEQ ID NO 18
<211> LENGTH: 33
<212> TYPE: DNA
<213> ORGANISM: Artificial Sequence
<220> FEATURE:
<223> OTHER INFORMATION: synthetic DNA

<400> SEQUENCE: 18
ttcagttcta gactgggcca gagatgcagc acc                                    33

<210> SEQ ID NO 19
<211> LENGTH: 28
<212> TYPE: DNA
<213> ORGANISM: Artificial Sequence

```
<220> FEATURE:
<223> OTHER INFORMATION: synthetic DNA

<400> SEQUENCE: 19
ctcttgtcta gagcaacaga aatacaac                                              28

<210> SEQ ID NO 20
<211> LENGTH: 33
<212> TYPE: DNA
<213> ORGANISM: Artificial Sequence
<220> FEATURE:
<223> OTHER INFORMATION: synthetic DNA

<400> SEQUENCE: 20
tagcatcgcg gccgctggtc ggcttttctg cct                                        33

<210> SEQ ID NO 21
<211> LENGTH: 31
<212> TYPE: DNA
<213> ORGANISM: Artificial Sequence
<220> FEATURE:
<223> OTHER INFORMATION: synthetic DNA

<400> SEQUENCE: 21
ctcagagcgg ccgctggaat gtgcacacat c                                          31

<210> SEQ ID NO 22
<211> LENGTH: 561
<212> TYPE: DNA
<213> ORGANISM: Oryctolagus cuniculus

<400> SEQUENCE: 22
atggaagggg tccgacccct agaagagaat gtgggaaacg caccaaggcc aaggtttgag           60
agaaacaagc tattgctggt ggcctccgta gttcaggcac tggggctgct tctgtgcctc          120
acctacgtct gccagcactc ccatgctccc gaggtgtcac ttcagtatcc tccaattgaa          180
aatatcatga cacaacttca atcttaaca tcccatgagt gtgaagagga cagtttcatc           240
ctcccactcc aaaaaggga cggaaccatg gaagtgcaaa acaactcagt cgtcatccag           300
tgtgatggct tttatctcct gtctctgaag ggctacttct cccaggaggt cagcattagt          360
cttcactatc ggaagggtga ggagcccttc ccgatcctga agaagaccaa gtttgccaac          420
tccaacgtgg tgttaaaatt gggttacaaa gacaaagtct acctgaatgt gaccaccgac          480
agcgcctcct gcaagcagct cagtgtgaat gctggggagc tgattgtcat ccttcaaaat          540
cccggtgggt actgcgctcc c                                                    561

<210> SEQ ID NO 23
<211> LENGTH: 594
<212> TYPE: DNA
<213> ORGANISM: Mus musculus

<400> SEQUENCE: 23
atggaagggg aagggggttca accccctggat gagaatctgg aaaacggatc aaggccaaga          60
ttcaagtgga agaagacgct aaggctggtg gtctctggga tcaagggagc agggatgctt         120
ctgtgcttca tctatgtctg cctgcaactc tcttcctctc cggcaaagga ccctccaatc          180
caaagactca gaggagcagt taccagatgt gaggatgggc aactattcat cagctcatac          240
aagaatgagt atcaaactat ggaggtgcag aacaattcgg ttgtcatcaa gtgcgatggg          300
ctttatatca tctacctgaa gggctccttt ttccaggagg tcaagattga ccttcatttc          360
```

```
cgggaggatc ataatcccat ctctattcca atgctgaacg atggtcgaag gattgtcttc     420
actgtggtgg cctctttggc tttcaaagat aaagtttacc tgactgtaaa tgctcctgat     480
actctctgcg aacacctcca gataaatgat ggggagctga ttgttgtcca gctaacgcct     540
ggatactgtg ctcctgaagg atcttaccac agcactgtga accaagtacc actg           594
```

<210> SEQ ID NO 24
<211> LENGTH: 543
<212> TYPE: DNA
<213> ORGANISM: Vicugna pacos

<400> SEQUENCE: 24

```
atggaagggg tccaacccct ggacgggaat gtgggaaaca cgccagggcg agattctta      60 aggaacaagc tattactggt ggcctccgta attcaggggc tggggctgct cctgtgtctc    120
acttacatct gtctgcactt ctatgctcag gtgccagctg agtaccctcc aattcaaagt    180
atcagagtac agtttaccaa gtgtgaaaat gagaatggtt tcaccattgc atcctcaaac    240
aaggatggga ccatgaaggt gcaaacaac tcaatcatca tcagctgtga cggcttctat     300
ctcatctccc tgaagggcta cttctctcag gagctcagcc tcagccttca gtaccggaag    360
ggtcgggaac cctcttctc cctaagcaag gtcagaactg tcgacttcgt cacagtggcc     420
catctggctt tcaaggacat agtctacttg aatgtgagca ctcacagtac cacctgtgaa    480
gacatccagg tgaatggtgg ggaactgact ctcattcatc aaaatcccgg tggattctgt    540
gct                                                                  543
```

<210> SEQ ID NO 25
<211> LENGTH: 555
<212> TYPE: DNA
<213> ORGANISM: Ornithorhynchus anatinus

<400> SEQUENCE: 25

```
atggatgttg gacagcctct gggagaggca cctgccaagt gtgaatgtga agaagaact      60 ccaaagagac ccaagcttct gctggtgtcc tccatcctgc tgtggttagg tttgcttgtg    120
tgcctgatct acatctgctg ggatgcctgg caggcttctc aggacccaaa tgggcatcca    180
ggcggccatc agaacctaat ttttaaagca gatattggaa agtgtgaatc cggtgggaat    240
cacttaacca tccaagctgt taatcagtcc atgaaggtag aaaacaactt ggtcctcatc    300
ccttgtgatg gtccttattt ggtctacctg aaagtccact cgtccaagct cctcacaatc    360
acgattcgct atcgcaacgg cgaaaagctc tccgccttga atctctccaa cgatgtggat    420
tacgtcacag tggcttccct catgttcaag acaagctct ccctggaagt gactgacacc     480
cgcaactgca ctgagcacat tacaggtgaa ctaggcctca ttttgctggc acccaaaaag    540
tactgcagca acaac                                                     555
```

<210> SEQ ID NO 26
<211> LENGTH: 187
<212> TYPE: PRT
<213> ORGANISM: Oryctolagus cuniculus

<400> SEQUENCE: 26

```
Met Glu Gly Val Arg Pro Leu Glu Glu Asn Val Gly Asn Ala Pro Arg
  1               5                  10                  15

Pro Arg Phe Glu Arg Asn Lys Leu Leu Leu Val Ala Ser Val Val Gln
             20                  25                  30

Ala Leu Gly Leu Leu Leu Cys Leu Thr Tyr Val Cys Gln His Ser His
```

```
            35                  40                  45
Ala Pro Glu Val Ser Leu Gln Tyr Pro Pro Ile Glu Asn Ile Met Thr
 50                  55                  60
Gln Leu Gln Ile Leu Thr Ser His Glu Cys Glu Asp Ser Phe Ile
 65                  70                  75                  80
Leu Pro Leu Gln Lys Arg Asp Gly Thr Met Glu Val Gln Asn Asn Ser
                 85                  90                  95
Val Val Ile Gln Cys Asp Gly Phe Tyr Leu Leu Ser Leu Lys Gly Tyr
                100                 105                 110
Phe Ser Gln Glu Val Ser Ile Ser Leu His Tyr Arg Lys Gly Glu Glu
            115                 120                 125
Pro Phe Pro Ile Leu Lys Lys Thr Lys Phe Ala Asn Ser Asn Val Val
        130                 135                 140
Leu Lys Leu Gly Tyr Lys Asp Lys Val Tyr Leu Asn Val Thr Thr Asp
145                 150                 155                 160
Ser Ala Ser Cys Lys Gln Leu Ser Val Asn Ala Gly Glu Leu Ile Val
                165                 170                 175
Ile Leu Gln Asn Pro Gly Gly Tyr Cys Ala Pro
            180                 185
```

<210> SEQ ID NO 27
<211> LENGTH: 198
<212> TYPE: PRT
<213> ORGANISM: Mus musculus

<400> SEQUENCE: 27

```
Met Glu Gly Glu Gly Val Gln Pro Leu Asp Glu Asn Leu Glu Asn Gly
  1               5                  10                  15
Ser Arg Pro Arg Phe Lys Trp Lys Lys Thr Leu Arg Leu Val Val Ser
                 20                  25                  30
Gly Ile Lys Gly Ala Gly Met Leu Leu Cys Phe Ile Tyr Val Cys Leu
             35                  40                  45
Gln Leu Ser Ser Ser Pro Ala Lys Asp Pro Pro Ile Gln Arg Leu Arg
 50                  55                  60
Gly Ala Val Thr Arg Cys Glu Asp Gly Gln Leu Phe Ile Ser Ser Tyr
 65                  70                  75                  80
Lys Asn Glu Tyr Gln Thr Met Glu Val Gln Asn Asn Ser Val Val Ile
                 85                  90                  95
Lys Cys Asp Gly Leu Tyr Ile Ile Tyr Leu Lys Gly Ser Phe Phe Gln
                100                 105                 110
Glu Val Lys Ile Asp Leu His Phe Arg Glu Asp His Asn Pro Ile Ser
            115                 120                 125
Ile Pro Met Leu Asn Asp Gly Arg Arg Ile Val Phe Thr Val Val Ala
        130                 135                 140
Ser Leu Ala Phe Lys Asp Lys Val Tyr Leu Thr Val Asn Ala Pro Asp
145                 150                 155                 160
Thr Leu Cys Glu His Leu Gln Ile Asn Asp Gly Glu Leu Ile Val Val
                165                 170                 175
Gln Leu Thr Pro Gly Tyr Cys Ala Pro Glu Gly Ser Tyr His Ser Thr
            180                 185                 190
Val Asn Gln Val Pro Leu
        195
```

<210> SEQ ID NO 28
<211> LENGTH: 181

```
<212> TYPE: PRT
<213> ORGANISM: Vicugna pacos

<400> SEQUENCE: 28
```

| | | | | | | | | | | | | | | |
|---|---|---|---|---|---|---|---|---|---|---|---|---|---|---|
|Met|Glu|Gly|Val|Gln|Pro|Leu|Asp|Gly|Asn|Val|Gly|Asn|Thr|Pro|Gly|
|1| | | |5| | | | |10| | | | |15|

Arg Arg Phe Leu Arg Asn Lys Leu Leu Leu Val Ala Ser Val Ile Gln
                20                  25                  30

Gly Leu Gly Leu Leu Cys Leu Thr Tyr Ile Cys Leu His Phe Tyr
            35                  40                  45

Ala Gln Val Pro Ala Glu Tyr Pro Pro Ile Gln Ser Ile Arg Val Gln
 50                  55                  60

Phe Thr Lys Cys Glu Asn Glu Asn Gly Phe Thr Ile Ala Ser Ser Asn
65                  70                  75                  80

Lys Asp Gly Thr Met Lys Val Gln Asn Asn Ser Ile Ile Ile Ser Cys
                85                  90                  95

Asp Gly Phe Tyr Leu Ile Ser Leu Lys Gly Tyr Phe Ser Gln Glu Leu
            100                 105                 110

Ser Leu Ser Leu Gln Tyr Arg Lys Gly Arg Glu Pro Leu Phe Ser Leu
        115                 120                 125

Ser Lys Val Arg Thr Val Asp Phe Val Thr Val Ala His Leu Ala Phe
130                 135                 140

Lys Asp Ile Val Tyr Leu Asn Val Ser Thr His Ser Thr Thr Cys Glu
145                 150                 155                 160

Asp Ile Gln Val Asn Gly Gly Glu Leu Thr Leu Ile His Gln Asn Pro
                165                 170                 175

Gly Gly Phe Cys Ala
            180

```
<210> SEQ ID NO 29
<211> LENGTH: 185
<212> TYPE: PRT
<213> ORGANISM: Ornithorhynchus anatinus

<400> SEQUENCE: 29
```

Met Asp Val Gly Gln Pro Leu Gly Glu Ala Pro Ala Lys Cys Glu Cys
1               5                   10                  15

Glu Arg Arg Thr Pro Lys Arg Pro Lys Leu Leu Leu Val Ser Ser Ile
                20                  25                  30

Leu Leu Trp Leu Gly Leu Leu Val Cys Leu Ile Tyr Ile Cys Trp Asp
            35                  40                  45

Ala Trp Gln Ala Ser Gln Asp Pro Asn Gly His Pro Gly Gly His Gln
 50                  55                  60

Asn Leu Ile Phe Lys Ala Asp Ile Gly Lys Cys Glu Ser Gly Gly Asn
65                  70                  75                  80

His Leu Thr Ile Gln Ala Val Asn Gln Ser Met Lys Val Glu Asn Asn
                85                  90                  95

Leu Val Leu Ile Pro Cys Asp Gly Pro Tyr Leu Val Tyr Leu Lys Val
            100                 105                 110

His Ser Ser Lys Leu Leu Thr Ile Thr Ile Arg Tyr Arg Asn Gly Glu
        115                 120                 125

Lys Leu Ser Ala Leu Asn Leu Ser Asn Asp Val Asp Tyr Val Thr Val
130                 135                 140

Ala Ser Leu Met Phe Lys Asp Lys Leu Ser Leu Glu Val Thr Asp Thr
145                 150                 155                 160

```
Arg Asn Cys Thr Glu His Ile Thr Gly Glu Leu Gly Leu Ile Leu Leu
            165                 170                 175

Ala Pro Lys Lys Tyr Cys Ser Asn Asn
            180                 185

<210> SEQ ID NO 30
<211> LENGTH: 5
<212> TYPE: PRT
<213> ORGANISM: Artificial Sequence
<220> FEATURE:
<223> OTHER INFORMATION: synthetic protein

<400> SEQUENCE: 30

Gly Gly Gly Gly Ser
 1               5

<210> SEQ ID NO 31
<211> LENGTH: 15
<212> TYPE: PRT
<213> ORGANISM: Artificial Sequence
<220> FEATURE:
<223> OTHER INFORMATION: synthetic protein

<400> SEQUENCE: 31

Gly Gly Gly Gly Ser Gly Gly Gly Gly Ser Gly Gly Gly Gly Ser
 1               5                  10                  15
```